(12) United States Patent
Depaz et al.

(10) Patent No.: US 10,125,195 B2
(45) Date of Patent: Nov. 13, 2018

(54) STABLE ANTI-IFNAR1 FORMULATION

(71) Applicant: ASTRAZENECA AB, Sodertalje (SE)

(72) Inventors: Roberto Depaz, Gaithersburg, MD (US); Natalie DeJesus, Gaithersburg, MD (US); Jared Bee, Gaithersburg, MD (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 15/240,224

(22) Filed: Aug. 18, 2016

(65) Prior Publication Data
US 2017/0051066 A1 Feb. 23, 2017

Related U.S. Application Data

(60) Provisional application No. 62/207,164, filed on Aug. 19, 2015.

(51) Int. Cl.
C07K 16/00 (2006.01)
A61K 39/395 (2006.01)
C07K 16/28 (2006.01)
A61K 9/00 (2006.01)

(52) U.S. Cl.
CPC ........ C07K 16/2866 (2013.01); A61K 9/0019 (2013.01); A61K 39/39591 (2013.01)

(58) Field of Classification Search
CPC .............. C07K 16/2866; A61K 9/0019; A61K 395/39591
See application file for complete search history.

(56) References Cited

U.S. PATENT DOCUMENTS

| 6,713,609 | B1* | 3/2004 | Chuntharapai .... C07K 16/2866 424/143.1 |
| 7,662,381 | B2* | 2/2010 | Cardarelli .......... C07K 16/2866 424/143.1 |
| 2015/0239970 | A1* | 8/2015 | Bee ...................... A61K 9/0019 424/158.1 |

FOREIGN PATENT DOCUMENTS

| WO | WO 2009/070642 A1 | 6/2009 |
| WO | WO 2010/056804 A1 | 5/2010 |
| WO | WO 2014/186350 A1 | 11/2014 |
| WO | WO 2015/063180 A1 | 5/2015 |

OTHER PUBLICATIONS

Peng et al, Molecular Basis for Antagonistic Activity of Anifrolumab, an Anti-interferon-a Receptor 1 Antibody, mAbs Jan. 15, 2015, vol. 7, No. 2; pp. 428-439.

* cited by examiner

Primary Examiner — Cherie M Stanfield

(57) ABSTRACT

The present invention relates to a stable, low viscosity antibody formulation, wherein the formulation comprises a high concentration of anti-INFAR1 antibody. In some embodiments, the invention relates in general to a stable antibody formulation comprising about 100 mg/mL to about 200 mg/mL of an antibody or fragment thereof that specifically binds human interferon alpha 1 (INFAR1); about 20 mM to about 80 mM of a lysine or a salt thereof; about 0.02% to about 0.06% of a surfactant; an uncharged excipient; and a formulation buffer. In some embodiments, the invention is directed to a container, dosage form and/or kit. In some embodiments, the invention is directed to a method of making and using the stable antibody formulation.

3 Claims, 5 Drawing Sheets

Specification includes a Sequence Listing.

SEQUENCE LISTING

<160> NUMBER OF SEQ ID NOS: 2

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Cys Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Leu Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys
            100                 105

STABLE ANTI-IFNAR1 FORMULATION

CROSS-REFERENCE TO RELATED APPLICATIONS

This application claims benefit under 35 U.S.C. § 119(e) of U.S. Provisional Application No. 62/207,164, filed Aug. 19, 2015, which is incorporated by reference herein in its entirety for all purposes.

REFERENCE TO THE SEQUENCE LISTING

This application incorporates by reference a Sequence Listing submitted with the application via EFS-Web as a text filed entitled "IFNAR-350US1_SL.txt" created on Aug. 18, 2016, and having a size of 2.490 KB.

BACKGROUND OF THE INVENTION

Field of the Invention

The present invention relates to a stable, low viscosity antibody formulation, wherein the formulation comprises a high concentration of an antibody that specifically binds interferon alpha receptor 1 (IFNAR1) or an antigen-binding fragment thereof. In embodiments, the antibody formulation comprises anifrolumab or an antigen-binding fragment thereof.

In some embodiments, the invention relates to a stable antibody formulation comprising about 100 mg/mL to about 200 mg/mL of an antibody or fragment thereof that specifically binds IFNAR1, about 25 mM to about 130 mM of lysine or a lysine salt; an uncharged excipient; a surfactant; and a formulation buffer. In some embodiments, the invention is directed to a container, dosage form and kit. In some embodiments, the invention is directed to a method of making and using the stable antibody formulation.

Background

Antibodies have been used in the treatment of various diseases and conditions due to their specificity of target recognition, thereby generating highly selective outcomes following systemic administration. In order for antibodies to remain effective, they must maintain their biological activity during their production, purification, transport and storage. New production and purification techniques have been developed to provide for large amounts of highly purified monoclonal antibodies to be produced. However, challenges still exist to stabilize these antibodies for transport and storage, and yet even more challenges exist to provide the antibodies in a dosage form suitable for administration.

Denaturation, aggregation, contamination, and particle formation can be significant obstacles in the formulation and storage of antibodies. Due to the wide variety of antibodies, there are no universal formulations or conditions suitable for storage of all antibodies. Optimal formulations of one antibody are often specific to that antibody. Additionally, antibody formulations may need to be further tailored to a specific antibody depending on the concentration of the antibody, and/or a desired physical property, e.g., viscosity, of the antibody formulation. Antibody storage formulations are often a significant part of the research and development process for a commercial antibody.

Various methods have been proposed to overcome the challenges associated with antibody stability. For example, in some instances, the antibody is often lyophilized, and then reconstituted shortly before administration. However, reconstitution adds an additional step to the administration process, and could introduce contaminants to the formulation. Additionally, reconstituted antibodies could suffer from aggregation and particle formation. Thus, a need exists to provide stable antibody formulations that can overcome the challenges associated with transport and storage.

SUMMARY OF THE INVENTION

The present invention relates to a stable, low viscosity antibody formulation, wherein the formulation comprises a high concentration of anti-interferon alpha receptor 1 antibody or an antigen binding fragment thereof. In some embodiments, the invention relates in general to a stable antibody formulation comprising about 100 mg/mL to about 200 mg/mL of an antibody that specifically binds IFNAR1 or fragment thereof, about 25 mM to about 130 mM lysine or a lysine salt; an uncharged excipient, a surfactant; and a formulation buffer.

In embodiments, the invention is directed to an antibody formulation comprising about 100 mg/mL to about 200 mg/mL anifrolumab or an antigen binding fragment thereof; about 40 mM to about 60 mM lysine HCl; about 100 mM to about 160 mM trehalose dihydrate; about 0.02% to about 0.1% polysorbate 80; about 15 mM to about 35 mM histidine/histidine HCl, wherein the formulation is at a pH of from about 5.5 to 6.5.

In additional embodiments, the invention is directed to an antibody formulation comprising about 145 mg/mL to about 155 mg/mL anifrolumab or an antigen binding fragment thereof; about 45 mM to about 55 mM lysine HCl; about 120 mM to about 140 mM trehalose dihydrate; about 0.04% to about 0.08% polysorbate 80; and about 20 mM to about 30 mM histidine/histidine HCl, wherein the formulation is at a pH of from about 5.8 to about 6.1.

In some embodiments, the invention is directed to an antibody formulation comprising: about 150 mg/mL anifrolumab or an antigen binding fragment thereof; about 50 mM lysine HCl; about 130 mM trehalose dihydrate; about 0.05% polysorbate 80; and about 25 mM histidine/histidine HCl, wherein the formulation is at a pH of about 5.9.

In some embodiments, the invention is directed to an antibody formulation comprising: 150 mg/mL anifrolumab or an antigen binding fragment thereof; 50 mM lysine HCl; 130 mM trehalose dihydrate; 0.05% polysorbate 80; 25 mM histidine/histidine HCl, wherein the formulation is at a pH of about 5.9.

In additional embodiments, the invention is directed to an antibody formulation comprising: 150 mg/mL anifrolumab; 50 mM lysine HCl; 130 mM trehalose dihydrate; 0.05% polysorbate 80; 25 mM histidine/histidine HCl, wherein the formulation is at a pH of 5.9.

In some embodiments, the invention is directed to a pharmaceutical unit dosage form suitable for parenteral administration to a human which comprises any one of the antibody formulations described herein in a suitable container.

In some embodiments, the invention is directed to a kit comprising any antibody formulation described herein, a container as described herein, a unit dosage form as described herein, or a pre-filled syringe as described herein.

In some embodiments, the invention is directed to a method of producing a stable antibody formulation, the method comprising: purifying an antibody to about 100 mg/mL to about 200 mg/mL of an anti-IFNAR antibody or antigen-binding fragment thereof, placing the isolated antibody in a stabilizing formulation to form the stable antibody formulation, wherein the resulting stable antibody formulation comprises: about 100 mg/mL to about 200 mg/mL of the antibody; about 25 mM to about 130 mM of lysine or a lysine salt; about 100 mM to about 150 mM uncharged excipient; about 0.02% to about 0.1% of a surfactant; and a formulation buffer.

In some embodiments, the invention is directed to a method of treating a type I IFN-mediated disease or disorder in a subject in need thereof, the method comprising administering a therapeutically effective amount of the antibody formulation of any one of the antibody formulations described herein.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION OF THE INVENTION

Definitions

Figure 1:
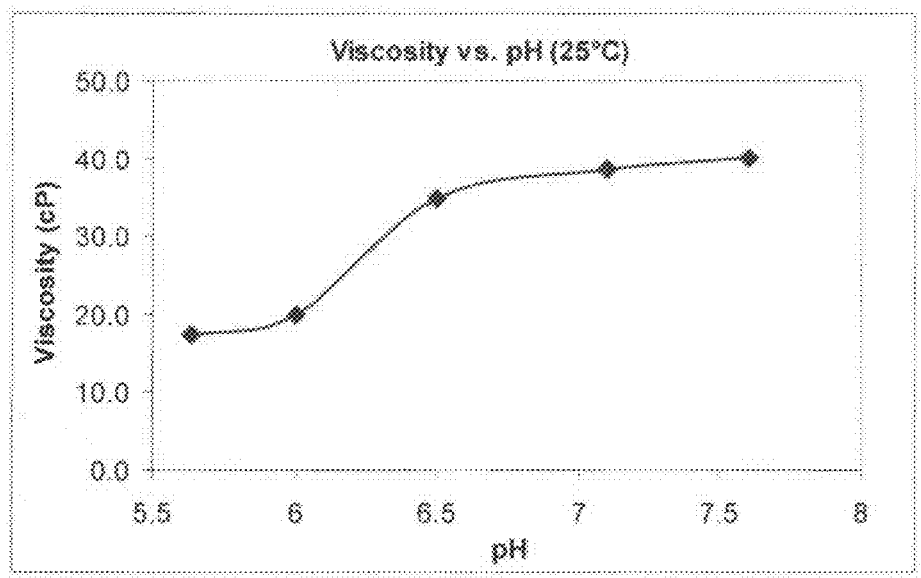
FIG. 1 shows viscosity as a function of pH in a high throughput screening bead-based method.

Before describing the present invention in detail, it is to be understood that this invention is not limited to specific compositions or process steps, as such can vary. It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A," (alone) and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Throughout the present disclosure, all expressions of percentage, ratio, and the like are "by weight" unless otherwise indicated. As used herein, "by weight" is synonymous with the term "by mass," and indicates that a ratio or percentage defined herein is done according to weight rather than volume, thickness, or some other measure.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

It is understood that wherever embodiments are described herein with the language "comprising," otherwise analogous embodiments described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "injection force" is the amount of pressure (in Newtons) required to pass the antibody formulation through a needle.

As used herein, the term "autoimmune disease" refers to a disorder, disease state or condition associated with the formation of autoantibodies reactive with the patient's own cells to form antigen-antibody complexes. The term "autoimmune disease" includes conditions such as, e.g., systemic lupus erythematosus, as well as those disorders which are triggered by a specific external agent, e.g., acute rheumatic fever. Examples of autoimmune disorders include, but are not limited to, autoimmune hemolytic anemia, autoimmune hepatitis, Berger's disease, chronic fatigue syndrome, Crohn's disease, dermatomyositis, fibromyalgia, Graves' disease, Hashimoto's thyroiditis, idiopathic thrombocytopenia purpura, lichen planus, multiple sclerosis, myasthenia gravis, psoriasis, rheumatic fever, rheumatoid arthritis, scleroderma, Sjogren's syndrome, systemic lupus erythematosus, type 1 diabetes, ulcerative colitis, and vitiligo. In specific aspects, the autoimmune disease is systemic lupus erythematosus (SLE), scleroderma (SSe), myositis, or lupus nephritis.

The terms "Interferon alpha receptor-1," "IFNARI," and "IFNAR" are used interchangeably, and include variants, isoforms, species homologs of human IFNAR1, and analogs having at least one common epitope with IFNARI. See, e.g., de Weerd et al., J. Bioi. Chem. 282:20053-20057 (2007). Accordingly, human antibodies specific for human IFNARI, in certain cases, cross-react with IFNARI from species other than human, or other proteins which are structurally related to human IFNAR1 (e.g., human IFNAR1 homologs). In other cases, the antibodies can be completely specific for human IFNAR1 and not exhibit species or other types of cross-reactivity. The complete cDNA sequence of human IFNAR1 has the Genbank accession number NM 000629.

The terms "type I interferon" or "type I IFN" as used herein refer to members of the type I interferon family of molecules that are ligands for IFNAR1 (i.e., members of the type I interferon family of molecules that are capable of binding IFNAR1). Examples of type I interferon ligands are interferon alpha 1, 2a, 2b, 4, 5, 6, 7, S, 10, 14, 16, 17, 21, interferon beta and interferon omega.

The term "type I IFN-mediated disease or disorder" refers to any type I IFN or IFN a inducible disease, disorder, or condition that exhibits a type I IFN pharmacodynamic ("PD") marker expression profile or gene signature (type I IFN GS). A PD marker expression profile and a gene signature will be understood to be equivalent. These diseases, disorders, or conditions include those with an autoimmune component such as systemic lupus erythematosus (SLE), scleroderma, lupus nephritis, o myositis. A type I IFN-mediated disease or disorder can be treated by administering a small molecule or a biological agent, e.g., an antibody or an antigen binding fragment thereof. If the therapeutic agent is a biological agent, it may be an antibody specific for any subtype(s) of type I IFN or IFNα. For instance, the antibody may be specific for any one of IFNα1, IFNα2, IFNα4, IFNα5, IFNα6, IFNα7, IFNα8, IFNα10, IFNα14, IFNα17, IFNα21, IFNβ, or IFNω. Alternatively, the antibody may be specific for any two, any three, any four, any five, any six, any seven, any eight, any nine, any ten, any eleven, any twelve type I IFN or iFNα subtypes. If the antibody is specific for more than one type I IFN subtype, the antibody may be specific for IFNα1, IFNα2, IFNα4, IFNα5, IFNα8, IFNα10, and IFNα21; or it may be specific for IFNα1, IFNα2, IFNα4, IFNα5, IFNα8, and IFNα10; or it may be specific for IFNα1, IFNα2, IFNα4, IFNα5, IFNα8, and IFNα21; or it may be specific for IFNα1, IFNα2, IFNα4, IFNα5, IFNα10, and IFNα21. A therapeutic agent that modulates IFNα activity may neutralize IFNα activity. A type I IFN-mediated disease or disorder can also be treated with antibodies specific for a type I IFN receptor, e.g., IFNAR1. In some aspects, anti-IFNAR1 antibodies can cross-react with IFNAR1 from species other than human. In other aspects, the anti-IFNAR1 antibodies can be specific for IFNAR1 only and not exhibit species or other types of cross-reactivity. In some aspects, the anti-IFNAR1 antibodies exhibit reduced binding affinities for FC ligands and have reduced or ablated effector function (ADCC and/or CDC), reduced or ablated binding to Fc ligands, or reduced or ablated toxicities as compared to an unmodified antibody.

The term "MEDI-546" refers to an Fc-modified version of the anti-IFNAR 9D4 antibody described in U.S. Pat. No. 7,662,381. The terms "MEDI-546" and "anifrolumab" are used interchangeably herein. The sequence of MEDI-546 is described in U.S. 2011-0059078. MEDI-546 comprises a combination of three mutations: L234F, L235E, and P331S, wherein the numbering is according to the EU index as set forth in Kabat, introduced into the lower hinge and CH2 domain of human IgG 1, which cause a decrease in their binding to human FcγRI (CD64), FcγRIIA (CD32A), FcγRIII (CD16) and C1q. See, e.g., U.S. 2011/0059078 and Oganesyan et al. *Acta Crystallographica* D 64:700-704 (2008), which are hereby incorporated by reference in their entireties. The VH and Vκ sequences of MEDI-546 are shown in TABLE 1.

TABLE 1

| MEDI-546 VH (SEQ ID NO: 1) | EVQLVQSGAEVKKPGESLKISCKGSGYIFTNYWIAWV RQMPGKCLESMGIIYPGDSDIRYSPSFQGQVTISADK SITTAYLQWSSLKASDTAMYYCARHDIEGFDYWGRGT LVTVSS |
|---|---|
| MEDI-546 Vκ (SEQ ID NO: 2) | EIVLTQSPGTLSLSPGERATLSCRASQSVSSSFFAWY QQKPGQAPRLLIYGASSRATGIPDRLSGSGSGTDFTL TITRLEPEDFAVYYCQQYDSSAITFGQGTRLEIK |

The term "antibody or antigen-binding fragment thereof that modulates type I IFN activity" refers to an antibody (see infra) in its broadest sense capable of modulating type I IFN activity in a patient. The term "modulating" as used herein includes the inhibition or suppression of a type I IFN activity as well as the induction or enhancement of a type I IFN activity. In specific aspects, the type I IFN activity is IFNα activity. In some aspects, the suppression of a type IFN GS is a suppression of a type I IFN activity. In some aspects, the antibody or antigen-binding fragment thereof is monoclonal. In specific aspects, the antibody or antigen-binding fragment thereof that modulates type I IFN activity specifically binds to a type I IFN receptor such as IFNAR1. In some specific aspects, the antibody or antigen binding fragment thereof specifically binds to subunit 1 of IFNAR1.

The term "antibody" is used herein in its broadest sense and includes, e.g., monoclonal antibodies, polyclonal antibodies, multivalent antibodies, multispecific antibodies, chimeric antibodies, and humanized antibodies. The term "antibody" includes whole antibodies. The term "antibody" also refers to a protein comprising at least two immunoglobulin heavy (H) chains and two immunoglobulin light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CHI, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FRI, CDRI, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding fragment" refers to one or more fragments of an antibody that retain the ability to specifically bind to an antigen (e.g., IFNAR). It has been shown that the antigen-binding function of an antibody can be performed by fragments of a full-length antibody. Examples of binding fragments encompassed within the term "antigen binding fragment" of an antibody include (i) a Fab fragment, a monovalent fragment consisting of the VL, VH, CL and CHI domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., (1989) *Nature*

341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci.* USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds IFNAR is substantially free of antibodies that specifically bind antigens other than IFNAR). An isolated antibody that specifically binds IFNAR can, however, have cross-reactivity to other antigens, such as IFNAR molecules from other species. Moreover, an isolated antibody can be substantially free of other cellular material and/or chemicals.

The term "monoclonal antibody" as used herein refer to a preparation of antibody molecules of single molecular composition. A monoclonal antibody displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or sitespecific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "antibody" as used herein also includes "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al, *Proc. Natl. Acad. Sci.* USA 81:6851-6855 (1984)).

Basic antibody structures in vertebrate systems are relatively well understood. See, e.g., Harlow et al. (1988) Antibodies: A Laboratory Manual (2nd ed.; Cold Spring Harbor Laboratory Press).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Bioi.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in TABLE 2 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 2

| CDR Definitions[1] | | |
|---|---|---|
|  | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in TABLE 2 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-IFNAR antibody or antigen-binding fragment, variant, or derivative thereof of the present disclosure are according to the Kabat numbering system.

The terms "treat" or "treatment" as used herein refer to both therapeutic treatment and prophylactic or preventative measures, wherein the object is to prevent or slow down (lessen) an undesired physiological change or disorder in a subject, such as the progression of an inflammatory disease or condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The term "treatment" also means prolonging survival as compared to expected survival if not receiving treatment. Those in need of treatment include those already with the condition or disorder as well as those prone to have the condition or disorder or those in which the condition or disorder is to be prevented.

Terms such as "treating" or "treatment" or "to treat" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented.

The terms "effective amount" or "amount effective to" or "therapeutically effective amount" includes reference to a dosage of a therapeutic agent sufficient to produce a desired result.

By "subject" or "patient" is meant any subject, particularly a mammalian subject, for whom diagnosis, prognosis, or therapy is desired. As used herein, the terms "subject" or "patient" include any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc. As used herein, phrases such as "a patient having a type I IFN-mediated disease or disorder" includes subjects, such as mammalian subjects, that would benefit from the administration of an antibody or antigenbinding fragment thereof that modulates type I IFN activity, e.g., for detection, imaging, or other diagnostic procedure, and/or from treatment, i.e., palliation or prevention of a disease, with such antibody or antigen-binding thereof.

Antibody Formulations

In embodiments, the present invention provides a stable antibody formulation comprising an anti-IFNAR1 antibody or antigen-binding fragment thereof. In embodiments, the anti-IFNAR1 antibody is anifrolumab. In embodiments, the formulations of the present invention comprise both anifrolumab and an antigen-binding fragment thereof.

In embodiments, the antibody formulations of the invention comprise an antibody or antigen-binding fragment thereof that comprises a VH domain sequence comprising from 0 to 5 amino acid substitutions from a reference VH having the amino acid sequence SEQ ID NO:1

In embodiments, the antibody formulations of the invention comprise an antibody or antigen-binding fragment comprises a Vκ domain comprising from 0-5 amino acid substitutions from a reference Vκ having the amino acid sequence SEQ ID NO:2.

In some embodiments, the antibody in the antibody formulation is purified prior to being added to the antibody formulation. The terms "isolate," and "purify" refer to separating the antibody from an impurity or other contaminants in the composition which the antibody resides, e.g., a composition comprising host cell proteins. In some embodiments, at least 50%, 70%, 80%, 90%, 95%, 98%, 99%, 99.5%, or 99.9% (w/w) of an impurity is purified from the antibody. For example, in some embodiments, purification of an antibody, e.g. anti-IFNAR1 antibody, would comprise separating the antibody from 99% (w/w) of the host cell proteins present originally in the composition.

In some embodiments, the terms "isolate," and "purify" refer to separating an antibody, e.g. anti-IFNAR1 antibody, from an impurity or other contaminants in the composition to an extent consistent with guidelines of a governmental organization, e.g., the World Health Organization or the United States Food and Drug Administration.

Methods of purifying an antibody are known to those of skill in the art. Suitable techniques for carrying out purification include various types of chromatography, such as affinity chromatography, hydrophobic interaction, ion exchange (such as cation exchange chromatography or mixed-mode chromatography), and filtration.

Affinity chromatography refers to a separation method whereby an antibody, by virtue of its specific binding properties, is bound to an affinity ligand for the antibody. The functional affinity ligand can be immobilized on a solid or semi-solid support so that when a composition comprising the antibody is passed over the ligand and the solid support, the antibody having a specific binding affinity to the ligand adsorbs to the ligand, and one or more other impurities are not adsorbed (or are bound at a lower affinity) and are separated from the antibody. Examples of impurities that do not typically bind (or do not bind well) include process-related impurities (e.g., host cell proteins, DNA, medium components) and some product-related impurities (e.g., antibody fragments). In some embodiments, the solid support comprising the ligand is washed one or more times with a buffer to remove additional impurities before the adsorbed antibody is removed from the ligand and the support. After one or more impurities have been removed, the adsorbed antibody can be removed (eluted) from the ligand and the support, resulting in isolation of the antibody from the original composition. Methods of removing the antibody from the ligand and support are dependent on the ligand and are known to those of skill in the art and can include, e.g., changes in environment, e.g., pH, addition or chaotropic agents or denaturants, or addition of commercially available elution buffers. In some embodiments, more than one affinity purification process can be employed on an antibody composition. Various affinity ligands are known in the art, including Protein A and Protein G (and combinations thereof). Immobilized ligands are commercially available. For example, Protein A affinity systems include MabSelect, MabSelect SuRe, MabSelect Xtra, MabSelect SuRe LX, Sepaharose CL-4B, ProSep vA, ProSep vA Ultra, and Ceramic HyperD.

Ion exchange chromatography includes cation exchange chromatography and mixed chromatography. Cation exchange chromatography refers to any method by which an antibody and some impurity or impurities can be separated based on charge differences using a cation exchange matrix. A cation exchange matrix generally comprises covalently bound, negatively charged groups. Weak or strong cation exchange resins may be employed. Commonly, strong cation exchange resins comprise supported organic groups comprising sulphonic acid or sulphonate groups, depending upon the pH. Weak cation exchanger resins commonly comprise supported organic groups comprising carboxylic acid or carboxylate groups, depending upon the pH. In certain embodiments, multimodal cation exchange resins can be used, which incorporate additional binding mechanisms as well as the ionic interactions, for example one or more of hydrogen bonding interactions and hydrophobic interactions. Examples of suitable cation exchange resins are well known in the art, and can include, but are not limited to Fractogel, carboxymethyl (CM), sulfoethyl (SE), sulfopropyl (SP), phosphate (P) and sulfonate (S), PROPAC WCX-10™ (Dionex), Capto S, S-Sepharose FF, Fractogel EMD $SO_3M$, Toyopearl Megacap II SP 550C, Poros 50 HS, and SP-sepharose matrix. In some embodiments, more than one cation exchange chromatography process can be employed on the composition.

Mixed mode chromatography refers to a method that utilizes more than one form of interaction between the stationary phase and analytes in order to achieve their separation from impurities (e.g., process-related impurities, such as host-cell proteins, DNA, and/or endogenous or adventitious viruses). Examples of suitable anion exchange matrices are known in the art, and can include, but are not limited to, Capto Adhere, Sartobind Q, Natrix Q, Chromasorb Q, and Mustang Q.

In some embodiments, additional filtration steps can be used to remove impurities. For example, in some embodiments nanofiltration or ultrafiltration is used. Nanofiltration comprises passing the composition through a matrix having a pore size of, e.g., less than 75 nm, less than 50 nm, and even less than 15 nm, to separate impurities, e.g., viruses, from the antibody. Commercially available nanofilters and ultrafilters that can be employed are manufactured by various vendors such as Millipore Corporation (Billerica, Mass., e.g., Viresolve Pro and Viresolve Pro+), Pall Corporation (East Hills, N.Y.), GE Healthcare Sciences (Piscataway, N.J.), and Sartorius Corporation (Goettingen, Germany).

In some embodiments, the antibody used in the formulations of the present invention, e.g., an anti-IFNAR, or antigen binding fragment thereof comprises the Kabat-defined VH sequence in SEQ ID NO:1 and the Kabat-defined Vκ of SEQ ID NO:2, wherein the antibody is in the formulation at a concentration of 10 mg/ml to 300 mg/ml, 30 mg/ml to 250 mg/ml, 50 mg/ml to 200 mg/ml, 100 mg/ml to 200 mg/ml, 125 mg/ml to 175 mg/ml, 130 mg/ml to 170 mg/mL, 135 mg/ml to 165 mg/mL, 140 mg/ml to 160 mg/mL, 145 mg/ml to 155 mg/mL, 130 mg/ml, 135 mg/ml, 140 mg/ml, 145 mg/ml, 146 mg/ml, 147 mg/ml, 148 mg/ml, 149 mg/ml, 150 mg/ml, 151 mg/ml, 152 mg/ml, 153 mg/ml, 154 mg/ml, 155 mg/ml, 156 mg/ml, 157 mg/ml, 158 mg/ml, 159 mg/ml or 160 mg/ml. In some embodiments, the antibody, is in concentration of about 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, 100 mg/ml, 125 mg/ml, 130 mg/ml, 140 mg/ml, 150 mg/ml, 160 mg/ml, 170 mg/ml, 180 mg/ml, 190 mg/ml, 200 mg/ml.

The antibody formulations of the present invention comprise lysine. Lysine is an essential amino acid having the following structure:

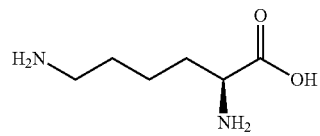

Lysine, as used herein, can include the free base form of lysine, as well as any and all salts thereof. In embodiments, the salt form of lysine is lysine acetate, lysine monochloride, lysine dichloride, lysine L-aspartate, and lysine L-glutamate In some embodiments, lysine includes a pharmaceutically acceptable salt thereof. For example, lysine would include lysine hydrochloride. Lysine, as used herein, also includes all enantiomers (e.g., L-lysine and S-lysine), and any combination of enantiomers (e.g., 50% L-lysine and 50% S-lysine; 90%-100% L-lysine and 10%-0% S-lysine, etc.). In some embodiments, the term "lysine" includes greater than 99% L-lysine and less than 1% S-alysine. In some embodiments, the term "lysine" includes a enantiomerically pure L-lysine. In some embodiments, lysine is a pharmaceutical grade lysine.

In embodiments, the antibody formulations of the present invention comprise about 10 to about 100 mM lysine, about 20 to about 90 mM lysine, about 30 mM lysine to about 80 mM lysine, about 40 to about 70 mM lysine, about 45 to about 65 mM lysine, about 45 to about 60 mM lysine, about 50 to about 55 mM lysine in the antibody formulation, e.g., an antibody formulation comprising 100 to 200 mg/mL antibody, or about 150 mg/mL antibody. In embodiments, the formulations of the present invention comprise about 50 mM lysine HCl in an antibody formulation comprising 100 to 200 mg/mL antibody, or about 150 mg/mL antibody, an uncharged excipient, a surfactant, and a formulation buffer.

The antibody formulations of the present invention can comprise an uncharged excipient. The term excipient refers to a pharmacologically inactive substance formulated with the antibody as described herein. In some embodiments, the excipient can assist in the prevention of denaturation or otherwise assist in stabilizing the antibody. Suitable excipients that may be used in the pharmaceutical compositions are known in the art. Examples can be taken e.g. from the handbook: Gennaro, Alfonso R.: "Remington's Pharmaceutical Sciences", Mack Publishing Company, Easton, Pa., 1990. In some embodiments, the excipient is an "uncharged" excipient, i.e., the excipient does not carry either a positive "+" or negative "−" charge. In some embodiments, the excipient is selected from the group consisting of fructose, glucose, mannose, sorbose, xylose, lactose, maltose, sucrose, dextran, pullulan, dextrin, cyclodextrins, soluble starch, trehalose, sorbitol, erythritol, isomalt, lactitol, maltitol, xylitol, glycerol, lactitol, hydroxyethyl starch, water-soluble glucans.

In some embodiments, the uncharged excipient is about 1 mM to about 1 M, about 2 mM to about 500 mM, about 5 mM to about 400 mM, about 10 mM to about 300 mM or about 20 mM to about 250 mM in the antibody formulation. In some embodiments, the uncharged excipient is about 30 mM to about 230 mM, about 40 mM to about 220 mM, about 50 mM to about 210 mM, about 60 mM to about 210 mM, about 70 mM to about 200 mM, about 80 mM to about 190 mM, about 90 mM to about 180 mM, about 100 mM to about 170 mM, about 110 mM to about 160 mM, about 120 mM to about 150 mM, about 125 mM to about 145 mM, about 125 mM to about 140 mM, about 120 mM, about 125 mM, about 130 mM, about 135 mM, about 140 mM, about 150 mM, about 160 mM, or about 170 mM in the antibody formulation, e.g., an antibody formulation comprising 100 to 200 mg/mL antibody. In one embodiment, the uncharged excipient is about 130 mM in the antibody formulation. In some embodiments, the uncharged excipient is about 50 mM to about 500 mM, about 100 mM to about 450 mM, about 110 mM to about 350 mM, about 120 mM, about 125 mM, about 130 mM, about 140 mM, or about 145 mM in the antibody formulation, e.g., an antibody formulation comprising 100 to 200 mg/mL antibody or about 150 mg/mL antibody. In one embodiment, the uncharged excipient is about 130 mM in the antibody formulation.

In some embodiments, the uncharged excipient is trehalose, as represented by the formula:

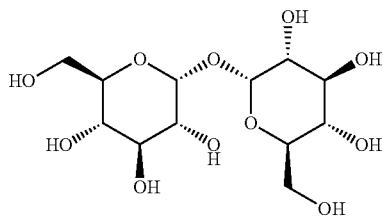 [SMILES: OC[C@H]1O[C@H](O[C@H]2O[C@H](CO)[C@@H](O)[C@H](O)[C@H]2O)[C@H](O)[C@@H](O)[C@@H]1O]

antibody. In one embodiment, trehalose is about 130 mM in the antibody formulation.

Various other components can be included in the antibody formulation. In some embodiments, the antibody formulation can comprise a buffer (e.g., histidine, acetate, phosphate or citrate buffer), and/or a stabilizer agent (e.g. human albumin), etc. In some embodiments, the antibody formulation can comprise pharmaceutically acceptable carriers, including, e.g., ion exchangers, alumina, aluminum stearate, lecithin, serum proteins, such as human serum albumin, buffer substances such as phosphates, sucrose, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, polyethylene-polyoxypropylene-block polymers, and polyethylene glycol.

In some embodiments, the antibody formulation further comprises a surfactant. In some embodiments, the surfactant is selected from the group consisting of Triton X-100, Tween 80, polysorbate 20, polysorbate 80, nonoxynol-9, polyoxamer, stearyl alcohol, sodium dodecyl sulfate, and sorbitan monostearate.

In some embodiments, the surfactant is polysorbate 80, i.e., polyoxyethylene (20) sorbitan monooleate, as represented by the formula:

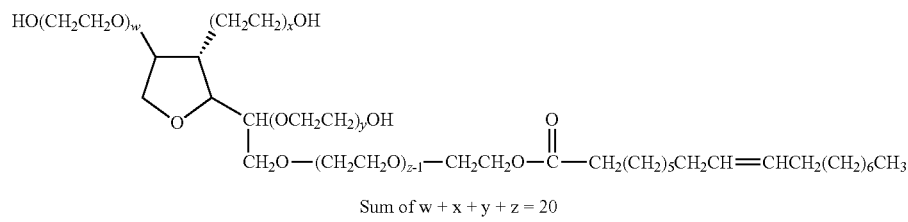

Sum of w + x + y + z = 20

In some embodiments, the trehalose is about 1 mM to about 1 M, about 2 mM to about 500 mM, about 5 mM to about 400 mM, about 10 mM to about 300 mM or about 20 mM to about 250 mM in the antibody formulation. In some embodiments, the trehalose is about 30 mM to about 230 mM, about 40 mM to about 220 mM, about 50 mM to about 210 mM, about 60 mM to about 210 mM, about 70 mM to about 200 mM, about 80 mM to about 190 mM, about 90 mM to about 180 mM, about 100 mM to about 170 mM, about 110 mM to about 160 mM, about 120 mM to about 150 mM, about 125 mM to about 145 mM, about 125 mM to about 140 mM, about 120 mM, about 125 mM, about 130 mM, about 135 mM, about 140 mM, about 150 mM, about 160 mM, or about 170 mM in the antibody formulation, e.g., an antibody formulation comprising 100 to 200 mg/mL antibody. In one embodiment, trehalose is about 130 mM in the antibody formulation. In some embodiments, trehalose is about 50 mM to about 500 mM, about 100 mM to about 450 mM, about 110 mM to about 350 mM, about 120 mM, about 125 mM, about 130 mM, about 140 mM, or about 145 mM in the antibody formulation, e.g., an antibody formulation comprising 100 to 200 mg/mL antibody or about 150 mg/mL Polysorbate 80 (PS-80) is available commercially from several commercial vendors, e.g., Alkest® TW 80 (Univar®), and Tween® 80 (Sigma-Aldrich®). Applicants have found that in some instances, controlling the concentration of PS-80 in the antibody formulation adds stability and reduces the amount of particle formation when stored for extended periods of time.

In some embodiments, PS-80 is about 0.01% to about 0.1%, about 0.02% to about 0.09%, about 0.02% to about 0.08%, about 0.03% to about 0.08%, about 0.04% to about 0.07%, about 0.05% to about 0.06%, about 0.02%, about 0.03%, about 0.04%, about 0.05%, about 0.06% about 0.07% of the antibody formulation, e.g., an antibody formulation comprising about 100 mg/mL to about 200 mg/mL antibody or about 150 mg/mL antibody. In some embodiments, PS-80 is about 0.05% in the antibody formulation.

In some embodiments, the antibody formulation further comprises histidine/histidine HCl buffer. In some embodiments, the antibody formulation comprises about 1 mM to about 100 mM, about 5 mM to about 80 mM histidine/histidine HCl buffer, about 10 mM to about 60 mM histidine/histidine HCl buffer, about 15 mM to about 50 mM histidine/histidine HCl buffer, about 15 mM to about 30 mM histidine/ histidine HCl buffer, or about 25 mM histidine/histidine HCl buffer in the antibody formulations of the present invention, e.g., an antibody formulation comprising 100 to 200 mg/mL antibody or about 150 mg/mL antibody. In one embodiment, histidine/histidine HCl buffer is about 25 mM in the antibody formulation.

In some embodiments, the invention is directed to an antibody formulation comprising: 150 mg/mL anifrolumab or an antigen binding fragment thereof; 50 mM lysine HCl; 130 mM uncharged excipient; 0.05% surfactant; 25 mM formulation buffer, wherein the formulation is at a pH of about 5.9.

In some embodiments, the invention is directed to an antibody formulation comprising: 150 mg/mL anifrolumab; 50 mM lysine HCl; 130 mM uncharged excipient; 0.05% surfactant; 25 mM formulation buffer, wherein the formulation is at a pH of about 5.9

In additional embodiments, the invention is directed to an antibody formulation comprising: 150 mg/mL anifrolumab; 50 mM lysine HCl; 130 mM trehalose dihydrate; 0.05% polysorbate 80; 25 mM histidine/histidine HCl, wherein the formulation is at a pH of 5.9.

In some embodiments, the invention is directed to a stable antibody formulation comprising: (a) about 100 mg/mL to about 200 mg/mL of an antibody or an antigen binding fragment thereof, wherein the antibody is anifrolumab, (b) about 0.02% to about 0.1% polysorbate-80, (c) about 100 mM to about 160 mM trehalose, (d) about 40 mM to about 60 mM L-lysine HCl, (e) and 15-35 mM histidine/histidine HCl. In embodiments, the formulation pH is about 5.5 to about 6.5.

In further embodiments, the invention is directed to a stable antibody formulation comprising: (a) about 145 mg/mL to about 155 mg/mL of an antibody or antigen binding fragment thereof, wherein the antibody is anifrulomab, (b) about 0.04% to about 0.08 polysorbate-80, (c) about 120-140 mM trehalose dihydrate, (d) about 45-55 mM L-lysine HCl, and (e) about 20-30 mM histidine/histidine HCl. In embodiments, the formulation pH is about 5.8 to about 6.1.

In further embodiments, the invention is directed to a stable antibody formulation comprising: (a) about 150 mg/mL of an antibody or antigen binding fragment thereof, wherein the antibody is anifrulomab, (b) about 0.05% polysorbate-80, (c) about 130 mM trehalose dihydrate, (d) about 50 mM L-lysine HCl, and (e) about 25 mM histidine/histidine HCl. In embodiments, the formulation pH is about 5.9.

In some embodiments, the invention is directed to an antibody formulation comprising: 150 mg/mL anifrolumab or an antigen binding fragment thereof; 50 mM lysine HCl; 130 mM trehalose dihydrate; 0.05% polysorbate 80; 25 mM histidine/histidine HCl, wherein the formulation is at a pH of about 5.9.

In additional embodiments, the invention is directed to an antibody formulation comprising: 150 mg/mL anifrolumab; 50 mM lysine HCl; 130 mM trehalose dihydrate; 0.05% polysorbate 80; 25 mM histidine/histidine HCl, wherein the formulation is at a pH of 5.9.

In some embodiments, various components can be omitted from the antibody formulation, or can be "substantially free" of that component. The term "substantially free" as used herein refers to an antibody formulation, said formulation containing less than 0.01%, less than 0.001%, less than 0.0005%, less than 0.0003%, or less than 0.0001% of the designated component.

The antibody formulations can have different osmolarity concentrations. Methods of measuring osmolarity of antibody formulations are known to those in the art, and can include, e.g., an osmometer (e.g., an Advanced Instrument Inc 2020 freezing point depression osmometer). In some embodiments, the formulation has an osmolarity of between 200 and 600 mosm/kg, between 260 and 500 mosm/kg, or between 300 and 450 mosm/kg.

The antibody formulation of the present invention can have various pH levels. In some embodiments, the pH of the antibody formulation is between 4 and 7, between 4.5 and 6.5, or between 5 and 6. In some embodiments, the pH of the antibody formulation is 5.0. In some embodiments, the pH of the antibody formulation is 6.0. In some embodiments, the pH of the antibody formulation is ≤7.0. Various means may be utilized in achieving the desired pH level, including, but not limited to the addition of the appropriate buffer.

The antibody formulations described herein have various viscosities. Methods of measuring viscosity of antibody formulations are known to those in the art, and can include, e.g., a rheometer (e.g., Anton Paar MCR301 Rheometer with either a 50 mm, 40 mm or 20 mm plate accessory). In some embodiments of the present invention, the viscosities were reported at a high shear limit of 1000 per second shear rate. In some embodiments, the antibody formulation has a viscosity of less than 20 centipoise (cP), less than 18 cP, less than 15 cP, less than 13 cP, or less than 11 cP. In some embodiments, the antibody formulation has a viscosity of less than 13 cP. One of skill in the art will appreciate that viscosity is dependent on temperature, thus, unless otherwise specified, the viscosities provided herein are measured at 25° C. unless otherwise specified.

The injection force is correlated with the amount of resistance provided by the antibody formulation when administering the antibody formulation to a subject. The injection force will be dependent on the gauge of the administering needle, as well as temperature. In some embodiments, the antibody formulation has an injection force of less than 15 N, 12 N, 10 N, or 8 N when passed through a 27 Ga spinal thin wall (STW) needle. In some embodiments, the antibody formulation has an injection force of less than 15 N, 12 N, 10 N, or 8 N when passed through a 29 Ga STW needle.

In additional embodiments, the antibody formulations of the present invention are an aqueous solution. In some embodiments, the antibody formulation has not been subjected to freezing temperatures, and/or have not been frozen, i.e., they have remained in a liquid state. In some embodiments, the antibody in the antibody formulation has not been subjected to lyophilization.

As used herein, the term stability generally is related to maintaining the integrity or to minimizing the degradation, denaturation, aggregation or unfolding of a biologically active agent such as a protein, peptide or another bioactive macromolecule. As used herein, "improved stability" generally means that, under conditions known to result in degradation, denaturation, aggregation or unfolding, the protein (e.g., antibody such as anifrolumab), peptide or another bioactive macromolecule of interest maintains greater stability compared to a control protein, peptide or another bioactive macromolecule.

In some embodiments, stability refers to an antibody formulation having low to undetectable levels of particle formation. The phrase "low to undetectable levels of particle formation" as used herein refers to samples containing less than 1000 particles/mL, less than 700 particles/ml, less than 650 particles/ml, less than 500 particles/ml, less than 400 particles/ml, less than 200 particles/ml, less than 100 particles/ml or less than 1 particle/ml as determined by HIAC analysis or visual analysis, wherein the particles detected are greater than 10 micron in size, after storage at about 40° C. for about 18 months. In some embodiments, no particles in the antibody formulation are detected, either by HIAC analysis or visual analysis.

In some embodiments, stability refers to reduced fragmentation of the antibody. In embodiments, the fragmentation rate of the antibody, e.g., anifrolumab, in the formulations of the invention is about 2.0 to 4.0 percent per month for 12 months as determined by HP-SEC analysis performed on an Agilent HPLC system with a TSK-Gel G3000 column. In embodiments, the fragmentation rate of the antibody, e.g., anifrolumab, in the formulations of the invention is about 2.0 to 4.0 percent per month for 6 months as determined by HP-SEC analysis performed on an Agilent HPLC system with a TSK-Gel G3000 column. In embodiments, the fragmentation rate of the antibody, e.g., anifrolumab, in the formulations of the invention is about 2.0 to 4.0 percent per month for 2 months as determined by HP-SEC analysis performed on an Agilent HPLC system with a TSK-Gel G3000 column. In embodiments, the fragmentation rate of the antibody, e.g., anifrolumab, in the formulations of the invention is about 3.0 to 4.0 percent per month for 2 months as determined by HP-SEC analysis performed on an Agilent HPLC system with a TSK-Gel G3000 column.

In further embodiments, stability refers to reduced aggregation of the antibody. In embodiments, the aggregation rate of the antibody formulations of the present invention containing, e.g., anifrolumab, is about 0.5 to 2.5% per month for 12 months as determined by HP-SEC analysis performed on an Agilent HPLC system with a TSK-Gel G3000 column. In embodiments, the aggregation rate of the antibody formulations of the present invention containing, e.g., anifrolumab, is about 0.5 to 2.5% per month for 6 months as determined by HP-SEC analysis performed on an Agilent HPLC system with a TSK-Gel G3000 column. In embodiments, the aggregation rate of the antibody formulations of the present invention containing, e.g., anifrolumab, is about 0.5 to 2.5% per month for 2 months as determined by HP-SEC analysis performed on an Agilent HPLC system with a TSK-Gel G3000 column. In additional embodiments, the aggregation rate of the antibody formulations of the present invention containing, e.g., anifrolumab, is about 1 to 2% per month for 2 months as determined by HP-SEC analysis performed on an Agilent HPLC system with a TSK-Gel G3000 column.

In further embodiments, stability refers to reduced purity losses. In embodiments, the purity loss rate of the antibody formulations of the present invention containing, e.g., anifrolumab, is about 3 to 5% per month for 12 months as determined by HP-SEC analysis performed on an Agilent HPLC system with a TSK-Gel G3000 column. In embodiments, the purity loss rate of the antibody formulations of the present invention containing, e.g., anifrolumab, is about 3 to 5% per month for 6 months as determined by HP-SEC analysis performed on an Agilent HPLC system with a TSK-Gel G3000 column. In additional embodiments, the purity loss rate of the antibody formulations of the present invention containing, e.g., anifrolumab, is about 3.5 to 4.5% per month for 2 months as determined by HP-SEC analysis performed on an Agilent HPLC system with a TSK-Gel G3000 column.

One of skill in the art will appreciate that stability of a protein is dependent on other features in addition to the composition of the formulation. For example, stability can be affected by temperature, pressure, humidity, pH, and external forms of radiation. Thus, unless otherwise specified, stability referred to herein is considered to be measured at 40° C., one atmosphere pressure, 50% relative humidity, pH of 6.0, and normal background levels of radiation. Stability of the antibody in the antibody formulation can be determined by various means. In some embodiments, the antibody stability is determined by size exclusion chromatography (SEC). SEC separates analytes (e.g., macromolecules such as proteins and antibodies) on the basis of a combination of their hydrodynamic size, diffusion coefficient, and surface properties. Thus, for example, SEC can separate antibodies in their natural three-dimensional conformation from antibodies in various states of denaturation, and/or antibodies that have been degraded. In SEC, the stationary phase is generally composed of inert particles packed into a dense three-dimensional matrix within a glass or steel column. The mobile phase can be pure water, an aqueous buffer, an organic solvent, mixtures of these, or other solvents. The stationary-phase particles have small pores and/or channels which will only allow species below a certain size to enter. Large particles are therefore excluded from these pores and channels, but the smaller particles are removed from the flowing mobile phase. The time particles spend immobilized in the stationary-phase pores depends, in part, on how far into the pores they can penetrate. Their removal from the mobile phase flow causes them to take longer to elute from the column and results in a separation between the particles based on differences in their size.

In some embodiments, SEC is combined with an identification technique to identify or characterize proteins, or fragments thereof. Protein identification and characterization can be accomplished by various techniques, including but not limited chromatographic techniques, e.g., high-performance liquid chromatography (HPLC), immunoassays, electrophoresis, ultra-violet/visible/infrared spectroscopy, raman spectroscopy, surface enhanced raman spectroscopy, mass spectroscopy, gas chromatography, static light scattering (SLS), Fourier Transform Infrared Spectroscopy (FTIR), circular dichroism (CD), urea-induced protein unfolding techniques, intrinsic tryptophan fluorescence, differential scanning calorimetry, and/or ANS protein binding.

In some embodiments, protein identification is achieved by high-pressure liquid chromatography. Various instruments, and apparatuses are known to those of skill in the art to perform HPLC. Generally HPLC involves loading a liquid solvent containing the protein of interest onto a separation column, in which the separation occurs. The HPLC separation column is filled with solid particles (e.g. silica, polymers, or sorbents), and the sample mixture is separated into compounds as it interacts with the column particles. HPLC separation is influenced by the liquid solvent's condition (e.g. pressure, temperature), chemical interactions between the sample mixture and the liquid solvent (e.g. hydrophobicity, protonation, etc.), and chemical interactions between the sample mixture and the solid particles packed inside of the separation column (e.g. ligand affinity, ion exchange, etc.).

In some embodiments, the SEC and protein identification occurs within the same apparatus, or simultaneously. For example, SEC and HPLC can be combined, often referred to as HP-SEC.

In some embodiments, the antibody formulation comprises about 100 mg/ml to about 200 mg/ml antibody or antigen binding fragment thereof, wherein the antibody is anifrolumab, wherein said formulation is stable upon storage at about 40° C. for 1 to 24 months. In some embodiments, the formulation is stable upon storage at about 25° C. for 1 to 18 months. In some embodiments, the formulation is stable upon storage at about 5° C. for 1 to 6 months. In some embodiments, the formulation is stable upon storage at about 5° C. for 1 to 3 months. In some embodiments, the formulation is stable upon storage at about 5° C. for 1 to 12 months. In some embodiments, the formulation is stable upon storage at about 5° C. for at least 18 months. In some embodiments, the formulation is stable upon storage at about 5° C. for at least 24 months, or 36 months.

The term "stable" can be relative and not absolute. Thus, in some embodiments the antibody is stable if less than 20%, less than 15%, less than 10%, less than 5% or less than 2% of the antibody is degraded, denatured, aggregated or unfolded as determined by HP-SEC when the antibody is stored at 2° C. to 8° C. for 6 months. In some embodiments, the antibody is stable if less than 20%, less than 15%, less than 10%, less than 5% or less than 2% of the antibody is degraded, denatured, aggregated or unfolded as determined by SEC HPLC when the antibody is stored at 2° C. to 8° C. for 12 months. In some embodiments, the antibody in the antibody formulation is stable if less than 20%, less than 15%, less than 10%, less than 5% or less than 2% of the antibody is degraded, denatured, aggregated or unfolded as determined by HP-SEC when the antibody is stored at 2° C. to 8° C. for 18 months. In some embodiments, the antibody in the antibody formulation is stable if less than 20%, less than 15%, less than 10%, less than 5% or less than 2% of the antibody is degraded, denatured, aggregated or unfolded as determined by SEC HPLC when the antibody is stored at 2° C. to 8° C. for 24 months.

In some embodiments, the antibody is stable if less than 20%, less than 15%, less than 10%, less than 5% or less than 2% of the antibody is degraded, denatured, aggregated or unfolded as determined by HP-SEC when the antibody is stored at 23° C. to 27° C. for 3 months. In some embodiments, the antibody is stable if less than 20%, less than 15%, less than 10%, less than 5% or less than 2% of the antibody is degraded, denatured, aggregated or unfolded as determined by HP-SEC when the antibody is stored at 23° C. to 27° C. for 6 months. In some embodiments, the antibody is stable if less than 20%, less than 15%, less than 10%, less than 5% or less than 2% of the antibody is degraded, denatured, aggregated or unfolded as determined by HP-SEC when the antibody is stored at 23° C. to 27° C. for 12 months. In some embodiments, the antibody is stable if less than 20%, less than 15%, less than 10%, less than 5% or less than 2% of the antibody is degraded, denatured, aggregated or unfolded as determined by HP-SEC when the antibody is stored at 23° C. to 27° C. for 24 months.

In some embodiments the antibody is stable if less than 6%, less than 4%, less than 3%, less than 2% or less than 1% of the antibody is degraded, denatured, aggregated or unfolded per month as determined by HP-SEC when the antibody is stored at 40° C. In some embodiments the antibody is stable if less than 6%, less than 4%, less than 3%, less than 2% or less than 1% of the antibody is degraded, denatured, aggregated or unfolded per month as determined by HP-SEC when the antibody is stored at 5° C.

In embodiments the antibody is stable if 1%, 2%, 3%, 4%, 5% or 6% (or about 1% to 6%) of the antibody is degraded, denatured, aggregated or unfolded per month for 1-3 months, 1 to 6 months, 1 to 12 months, 1 to 18 months, or 1 to 24 months as determined by HP-SEC when the antibody is stored at 5° C.

In some embodiments, the antibody formulations of the present invention can be considered stable if the antibody exhibits very little to no loss of the binding activity of the antibody (including antibody fragments thereof) of the formulation compared to a reference antibody as measured by antibody binding assays know to those in the art, such as, e.g., ELISAs, etc., over a period of 8 weeks, 4 months, 6 months, 9 months, 12 months or 24 months. In some embodiments, the antibody stored at about 40° C. for at least 1 month retains at least 80%, at least about 85%, at least about 90%, at least about 95%, at least about 98%, or at least about 99% of binding ability to an INFAR1 receptor polypeptide compared to a reference antibody which has not been stored. In some embodiments, the antibody stored at about 5° C. for at least 6 months retains at least 80%, at least about 85%, at least about 90%, at least about 95%, at least about 98%, or at least about 99% of binding ability to an INFAR1 receptor polypeptide compared to a reference antibody which has not been stored. In some embodiments, the antibody stored at about 40° C. for at least 1 month retains at least 95% of binding ability to an INFAR1 receptor polypeptide compared to a reference antibody which has not been stored. In some embodiments, the antibody stored at about 5° C. for at least 6 months retains at least 95% of binding ability to an INFAR1 receptor polypeptide compared to a reference antibody which has not been stored.

Applicants have found the antibody formulations provided herein result in greatly reduced particle formation as determined by visual inspection, micro-flow imaging (MFI), or size-exclusion chromatography (SEC).

In some embodiments, the formulation is substantially free of particles upon storage at about 40° C. for at least 1 month as determined by visual inspection. In some embodiments, the formulation is substantially free from particles upon storage at about 5° C. for at least 6 months, at least 9 months, at least 12 months, at least 15 months, at least 18 months, at least 24 months, or at least 36 months as determined by visual inspection.

In some embodiments, the antibody formulation of the present invention can be used for pharmaceutical purposes. Antibodies used in pharmaceutical applications generally must have a high level of purity, especially in regard to contaminants from the cell culture, including cellular protein contaminants, cellular DNA contaminants, viruses and other transmissible agents. See "WHO Requirements for the use of animal cells as in vitro substrates for the production of biologicals: Requirements for Biological Substances No. 50." No. 878. Annex 1, 1998. In response to concerns about contaminants, The World Health Organization (WHO) established limits on the levels of various contaminants. For example, the WHO recommended a DNA limit of less than 10 ng per dose for protein products. Likewise, the United States Food and Drug Administration (FDA) set a DNA limit of less than or equal to 0.5 pg/mg protein. Thus, in some embodiments, the present invention is directed to antibody formulations meeting or exceeding contaminant limits as defined by one or more governmental organizations, e.g., the United States Food and Drug Administration and/or the World Health Organization.

In some embodiments, the antibody formulation described herein is pharmaceutically acceptable. "Pharmaceutically acceptable" refers to an antibody formulation that is, within the scope of sound medical judgment, suitable for contact with the tissues of human beings and animals without excessive toxicity or other complications commensurate with a reasonable benefit/risk ratio.

Purity of the antibody formulations can vary. In some embodiments, the therapeutic antibody of interest, e.g., anti-IFNAR1 antibody, is greater than 90% (wt/wt) of the total polypeptides present in the antibody formulation. In some embodiments, the therapeutic antibody of interest, e.g., anti-IFNAR1 is greater than 95% (wt/wt), 98% (wt/wt), 99% (wt/wt), 99.5% (wt/wt) or 99.9% (wt/wt) of the total polypeptide present in the antibody formulation.

The invention further provides methods of treating a type I IFN-mediated disease or disorder in a subject in need thereof, by administering a therapeutically effective amount of the antibody formulation described herein. In embodiments, the disease or disorder is selected from the group consisting of systemic lupus erythematosus (SLE), insulin dependent diabetes mellitus, inflammatory bowel disease, multiple sclerosis, psoriasis, autoimmune thyroiditis, rheumatoid arthritis, glomerulonephritis, scleroderma, myositis and lupus nephritis. In further embodiments, the disease or disorder is an inflammatory bowel disease such as, Crohn's disease, ulcerative colitis, and Celiac's disease. In further embodiments, the disease or disorder is a pulmonary disease or disorder, such as systemic lupus erythematosus.

The antibody formulation of the present invention can be administered to a subject through various means. In some embodiments, the antibody formulation is suitable for parenteral administration, e.g., via inhalation (e.g., powder or aerosol spray), transmucosal, intravenous, subcutaneous, or intramuscular administration. In some embodiments, the formulation is an injectable formulation. In some embodiments, the invention is directed to a sealed container comprising any of the antibody formulations as described herein.

In some aspects, the present invention is directed to various pharmaceutical dosage forms. Various dosage forms could be applicable to the formulations provided herein. See, e.g., Pharmaceutical Dosage Form: Parenteral Medications, Volume 1, $2^{nd}$ Edition. In one embodiment, a pharmaceutical unit dosage of the invention comprises the antibody formulation in a suitable container, e.g. a vial or syringe. In one embodiment, a pharmaceutical unit dosage of the invention comprises an intravenously, subcutaneously, or intramuscularly delivered antibody formulation. In another embodiment, a pharmaceutical unit dosage of the invention comprises aerosol delivered antibody formulation. In a specific embodiment, a pharmaceutical unit dosage of the invention comprises a subcutaneously delivered antibody formulation. In another embodiment, a pharmaceutical unit dosage of the invention comprises an aerosol delivered antibody formulation. In a further embodiment, a pharmaceutical unit dosage of the invention comprises an intranasally administered antibody formulation.

The antibody formulations of the present invention can be prepared as unit dosage forms by preparing a vial containing an aliquot of the aqueous antibody formulation for a one-time use. For example, a unit dosage per vial may contain 1 ml, 2 ml, 3 ml, 4 ml, 5 ml, 6 ml, 7 ml, 8 ml, 9 ml, 10 ml, 15 ml, or 20 ml of different concentrations of an antibody that specifically binds to IFNAR1 receptor ranging from about 0.1 mg/ml to about 300 mg/ml. If necessary, these preparations can be adjusted to a desired concentration by adding a sterile diluent to each vial. In a specific embodiment, the aqueous antibody formulations of the present invention are formulated into single dose vials as a sterile liquid that contains about 2 mg/mL to about 20 mg/mL of an antibody or antigen binding fragment thereof, wherein the antibody is anifrolumab. In another specific embodiment, the aqueous antibody formulations of the present invention are formulated into single dose vials as a sterile liquid that contains about 100 mg/mL to about 200 mg/mL of an antibody or antigen binding fragment thereof, wherein the antibody is anifrolumab, about 45 to 55 mM lysine HCl, about 0.04% to about 0.08% polysorbate-80, about 120 mM to about 140 mM trehalose, and about 20-30 mM histidine/histidine HCl. In embodiments, the pH of the formulation is about 6. In one embodiment, the antibody of the invention is supplied at 140 to 160 mg/ml in 3 cc USP Type I borosilicate amber vials (West Pharmaceutical Services—Part No. 6800-0675). In another embodiment, the antibody of the invention is supplied at 150 mg/ml in 3 cc USP Type I borosilicate amber vials.

The antibody formulations of the present invention can be prepared as unit dosage forms by preparing a pre-filled syringe containing an aliquot of the aqueous antibody formulation for a one-time use. For example, a unit dosage per pre-filled syringe may contain 0.1 ml, 0.2 ml, 0.3 ml, 0.4 ml, 0.5 ml, 0.6 ml, 0.7 ml, 0.8 ml, 0.9 ml, 1 ml, 2 ml, 3 ml, 4 ml, 5 ml, 6 ml, 7 ml, 8 ml, 9 ml, 10 ml, 15 ml, or 20 ml of different concentrations of an antibody or antigen binding fragment thereof that specifically binds to an IFNAR1 polypeptide ranging from about 140 mg/ml to about 160 mg/ml. In a specific embodiment, the aqueous antibody formulations of the present invention are formulated into single dose pre-filled syringes as a sterile liquid that contains about 145 mg/mL to about 155 mg/mL of an antibody or antigen binding fragment thereof, wherein the antibody is anifrolumab, about 45 to 55 mM lysine HCl, about 0.04% to about 0.08% polysorbate-80, about 120 mM to about 140 mM trehalose, and about 20-30 mM histidine/histidine HCl. In embodiments, the pH of the formulation is about 6. In a specific embodiment, the aqueous antibody formulations of the present invention are formulated into single dose prefilled syringes as a sterile liquid that contains about 145 mg/mL to about 155 mg/mL of an antibody or antigen binding fragment thereof, wherein the antibody wherein the antibody is anifrolumab, about 45 to 55 mM lysine HCl, about 0.04% to about 0.08% polysorbate-80, about 120 mM to about 140 mM trehalose, and about 20-30 mM histidine/histidine HCl. In embodiments, the pH of the formulation is about 6.

Various dosage amounts can be administered in a single use. For example, in some embodiments 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2 mg, 3 mg, 4 mg, 5 mg, 6 mg, 7 mg, 8 mg, 9 mg, 10 mg, 12 mg, 14 mg, 16 mg, 18 mg, 20 mg, 30 mg, 40 mg, 50 mg, 70 mg, or 100 mg of antibody can be administered in a single dose.

Various types of syringes can be used. The syringe can be filled with the antibody formulation immediately prior to administration to a subject, e.g., less than 1 week, 1 day, 6 hours, 3 hours, 2 hours, 1 hour, 30 minutes, 20 minutes, or 10 minutes prior to administration to a subject. In some embodiments, the syringe is filled with the antibody formulation at the point of retail sale, or by the facility for which treatment of the subject occurs. In some embodiments, the syringe is pre-filled, e.g., the syringe is filled with the antibody formulation greater than 1 day, 2 days, 4 days, 1 week, 2 weeks, 1 month, 2 months, 3 months, 6 months, 12 months, 18 months, 24 months, 3 years, or 4 years prior to administration to a subject. In some embodiments, the pre-filled syringe comprises a needle, e.g., a 27 G regular wall needle, a 27 G thin wall needle, a 29 G regular wall needle, or a 29 G thin wall needle. In some embodiments, the pre-filled syringe comprises a 27 G spinal thin wall needle.

In some embodiments, any syringe suitable for administration to the desired subject can be used. In some embodiments, the syringe is a plastic syringe or a glass syringe. In some embodiments, the syringe is made of materials that are substantially free from tungsten. In some embodiments, the syringe is coated with silicone. In some embodiments, the pre-filled syringe comprises a plunger having a fluoropolymer resin disk. Examples of syringes can include, but are not limited to BD Hypak™ SCF 1 MLL 27 G1/2-5B BD260L WL, 0.4 mg silicon oil MDN with 27 G STW needle; Hypak™ for Biotech 1 ml Long (Becton Dickinson), with a Becton Dickinson Hypak 1 mL long plunger stopper 4023 Flurotec Daikyo Si1000 (Catalog #47271919); C3Pin; Hypak™ for Biotech 0.8 mg silicone oil (Becton Dickinson); and CZ syringes (West, Catalog #19550807).

The aqueous antibody formulations of the present invention may be sterilized by various sterilization methods, including sterile filtration, radiation, etc. In a specific embodiment, the difiltered antibody formulation is filter-sterilized with a presterilized 0.2 micron filter. Sterilized aqueous antibody formulations of the present invention may be administered to a subject to prevent, treat and/or manage an immune response, e.g. an inflammatory response.

The invention further provides pre-filled syringes comprising the antibody formulations of the captioned invention. In some embodiments, the pre-filled syringe comprises (a) about 100 mg/mL to about 200 mg/mL of an anti-IFNAR1 antibody, about 25 mM to 130 mM lysine or a lysine salt, an uncharged excipient, a surfactant, and a formulation buffer.

The invention further provides pre-filled syringes comprising the antibody formulations of the captioned invention. In some embodiments, the pre-filled syringe comprises (a) about 100 mg/mL to about 200 mg/mL anifrolumab or an antigen binding fragment thereof, about 40 to 60 mM lysine HCl, about 100 mM to about 160 mM trehalose dihydrate, 0.02% to about 0.1% polysorbate 80, and about 15 mM to about 35 mM histidine/histidine HCl. In embodiments, the pH of the formulation is about 5.5 to about 6.5.

The invention further provides pre-filled syringes comprising the antibody formulations of the captioned invention. In some embodiments, the pre-filled syringe comprises (a) about 145 mg/mL to about 155 mg/mL anifrolumab or an antigen binding fragment thereof, about 45 to 55 mM lysine HCl, 120 mM to about 140 mM trehalose dihydrate, 0.04% to about 0.08% polysorbate 80, and 20 mM to about 30 mM histidine/histidine HCl. In embodiments, the pH of the formulation is about 5.8 to 6.1.

The invention further provides pre-filled syringes comprising the antibody formulations of the captioned invention. In some embodiments, the pre-filled syringe comprises (a) about 150 mg/mL of an antibody or antigen binding fragment thereof, wherein the antibody is anifrolumab, about 50 mM lysine HCl, about 0.05% polysorbate-80, about 130 mM trehalose dihydrate, and about 25 mM histidine/histidine HCl. In embodiments, the pH of the formulation is about 5.9.

The invention further provides pre-filled syringes comprising the antibody formulations of the captioned invention. In some embodiments, the pre-filled syringe comprises (a) about 150 mg/mL of anifrolumab, about 50 mM lysine HCl, about 0.05% polysorbate-80, about 130 mM trehalose dihydrate, and about 25 mM histidine/histidine HCl. In embodiments, the pH of the formulation is about 5.9.

In a specific embodiment, the antibody formulations of the present invention are formulated into single dose pre-filled syringes as a sterile liquid that contains about 145 mg/mL to about 155 mg/mL of an antibody or antigen binding fragment thereof, wherein the antibody wherein the antibody is anifrolumab, about 45 to 55 mM lysine HCl, about 0.04% to about 0.08% polysorbate-80, about 120 mM to about 140 mM trehalose, and about 20-30 mM histidine/histidine HCl. In embodiments, the pH of the formulation is about 6.

In embodiments, the invention is directed to a prefilled syringe comprising an antibody formulation of the present invention, wherein the pre-filled syringe has an average glide force of between 1 and 20 N when equipped with a 27 Gauge spinal thin-wall (STW) needle. In embodiments, the invention is directed to a prefilled syringe comprising an antibody formulation of the present invention, wherein the pre-filled syringe has an average glide force of between 5 and 15 N when equipped with a 27 Gauge spinal thin-wall (STW) needle. In embodiments, the invention is directed to a prefilled syringe comprising an antibody formulation of the present invention, wherein the pre-filled syringe has an average glide force of about 8 N when equipped with a 27 Gauge spinal thin-wall (STW) needle.

In some embodiments, the invention is directed to a kit comprising any of the antibody formulations described herein, the containers described herein, the unit dosage forms described herein, or the pre-filled syringe described herein.

In some embodiments, the present invention can also be directed to a method of producing a stable antibody formulation comprising an antibody, the method comprising: (a) purifying an antibody or antigen binding fragment thereof to about 100 mg/mL to about 200 mg/mL, wherein the antibody is anifrolumab; and (b) placing the isolated antibody in a stabilizing formulation to form the stable antibody formulation, wherein the resulting stable antibody formulation comprises: (i) about 100 mg/mL to about 200 mg/mL of an antibody or antigen binding fragment thereof, wherein the antibody is anifrolumab, and (ii) about 25 mM to about 130 mM lysine or a lysine salt; (iii) about 100 mM to about 150 mM trehalose (iv) about 0.02% to about 0.1% polysorbate-80.

In some embodiments, the present invention can also be directed to a method of producing a stable antibody formulation comprising an antibody, the method comprising: (a) purifying an antibody or antigen binding fragment thereof to about 100 mg/mL to about 200 mg/mL, wherein the antibody is anifrolumab; and (b) placing the isolated antibody in a stabilizing formulation to form the stable antibody formulation, wherein the resulting stable antibody formulation comprises: about 100 mg/mL to about 200 mg/mL of the antibody; about 45 mM to about 55 mM lysine HCl of lysine or a lysine salt; about 100 mM to about 150 mM uncharged excipient; about 0.02% to about 0.1% of a surfactant; and a formulation buffer.

In some embodiments, the present invention can also be directed to a method of producing a stable antibody formulation comprising an antibody, the method comprising: (a) purifying an antibody or antigen binding fragment thereof to about 145 mg/mL to about 155 mg/mL, wherein the antibody is anifrolumab; and (b) placing the isolated antibody in a stabilizing formulation to form the stable antibody formulation, wherein the resulting stable antibody formulation comprises about 145 mg/mL to about 155 mg/mL of the antibody, about 25 mM to about 130 mM of lysine or a lysine salt; about 120 mM to about 140 mM trehalose dihydrate; about 0.04% to about 0.08% polysorbate 80; about 20 mM to about 30 mM histidine/histidine HCl, wherein the formulation is at a pH of about 5.8 to 6.1.

In some embodiments, the invention is directed to a method of making a stable antibody formulation, the method comprising (a) purifying an antibody or antigen binding fragment thereof to about 150 mg/mL, wherein the antibody is anifrolumab; and (b) placing the isolated antibody in a stabilizing formulation to form the stable antibody formulation, wherein the resulting stable antibody formulation comprises: (i) about 150 mg/mL mg/mL of an antibody or antigen binding fragment thereof, wherein the antibody is anifrolumab, and (ii) about 50 mM lysine HCl; (iii) about 130 mM trehalose, (iv) about 0.05% % polysorbate-80.

Although many aspects of the invention are directed to aqueous formulations, it should be noted for the purpose of equivalents that the antibodies or antibody formulations of the invention may be lyophilized if desired. Thus, the invention encompasses lyophilized forms of the formulations of the invention, or lyophilized antibodies which are later reconstituted into an aqueous form. In some embodiments, the invention is directed to a method of producing a reconstituted antibody or antigen-binding fragment thereof formulation comprising anifrolumab, the method comprising: (a) purifying the antibody from a cell culture; (b) lyophilizing the isolated antibody; (c) adding the lyophilized antibody to a aqueous solution to form a reconstituted antibody formulation, wherein the reconstituted antibody formulation comprises: (i) about 100 mg/mL to about 200 mg/mL of an antibody or antigen binding fragment thereof, wherein the antibody is anifrolumab, and (ii) about 45 to about 55 mM lysine HCl.

In some embodiments, the invention is directed to an antibody formulation comprising an antibody or an antigen binding fragment thereof wherein the antibody is anifrolumab, wherein the antibody formulation is essentially free of particles. In some embodiments, the term "essentially free of particles" refer to the absence of visible particles when viewed under a light box. In some embodiments, the term "essentially free of particles" is synonymous with the phrase "low to undetectable levels of particle formation" as described previously. In some embodiments, essentially free of particles refers to samples containing less than 30 particles/mL, less than 20 particles/ml, less than 20 particles/ml, less than 15 particles/ml, less than 10 particles/ml, less than 5 particles/ml, less than 2 particles/ml or less than 1 particle/ml wherein the particles are greater than 25 µm and the particle count is determined by HIAC analysis or visual analysis. In some embodiments, essentially free of particles refers to samples containing 1 to 50 particles/mL, 2 to 40 particles/ml, 3-30 particles/ml, 4 to 25 particles/ml, or 5 to 20 particles/ml wherein the particles are greater than 25 µm and the particle count is determined by HIAC analysis or visual analysis. In some embodiments, the term "visible particles" refers to particles greater than 25 µm.

In some embodiments, essentially free of particles refers to samples containing 1 to 200 particles/mL, 10 to 150 particles/ml, about 30 particles/ml to about 100 particles/ml, or 40 to 80 particles/ml, wherein the particles are greater than 5 µm and the particle count is determined by HIAC analysis or visual analysis. In some embodiments, the term "visible particles" refers to particles greater than 5 µm. In some embodiments, no particles in the antibody formulation are detected, either by HIAC analysis or visual analysis.

In some embodiments, the invention is directed to an antibody formulation comprising an antibody or antigen binding fragment thereof wherein the antibody is anifrolumab, wherein the antibody formulation is essentially free of particles for at least 1 month, at least 2 months, at least 3 months, at least 4 months, at least 5 months, at least 6 months, at least 8 months, at least 10 months, at least 12 months, or at least 18 months when stored at 38° to 42° C. In some embodiments, the invention is directed to an antibody formulation comprising an antibody or antigen binding fragment thereof, wherein the antibody is anifrolumab, wherein the antibody formulation is essentially free of particles for at least 1 month, at least 2 months, at least 3 months, at least 4 months, at least 5 months, at least 6 months, at least 8 months, at least 10 months, at least 12 months, at least 18 months, at least 24 months, at least 30 months, at least 36 months, or at least 48 months when stored at 2-6° C.

In some embodiments, the invention is directed to a method of purifying an antibody or antigen-binding fragment thereof wherein the antibody is anifrolumab, the method comprising (i) obtaining a cell culture comprising the antibody, (ii) performing affinity chromatography on the antibody, (iv) performing cation exchange on the antibody, (v) performing mixed mode chromatography on the antibody.

In some embodiments, the invention is directed to a method of purifying an antibody or antigen binding fragment thereof wherein the antibody is anifrolumab, the method comprising (i) obtaining a cell culture comprising the antibody, (ii) binding the antibody to a Protein A column, (iii) eluting the antibody from the Protein A column, (iv) performing cation exchange on the antibody, (v) performing mixed mode chromatography on the antibody. In some embodiments, the method of purifying an antibody further comprises a viral inactivation process. In some embodiments, the viral inactivation step is performed by lowering the pH to less than 4.0. In some embodiments, the method further comprises a diafiltration process. In some embodiments, the method further comprises a filtration process. In some embodiments, the filtration process is sufficient to remove active virus particles.

In some embodiments, the invention is directed to a method of treating a patient. In some embodiments, the method comprises administering the antibody formulations described herein, the containers described herein, the unit dosage forms described herein, or the pre-filled syringe described herein to a subject in need thereof.

In some embodiments, the invention is suitable for treatment of pulmonary disease or disorder by administering the antibody formulation described herein. In some embodiments, the invention is directed to a method of treating a patient with an eosinophilic disease or disorder by administering the antibody formulation described herein. In some embodiments, the invention is directed to a method of treating a pulmonary disease or disorder in a subject, the method comprising administering the antibody formulations described herein. In some embodiments, the invention is directed to a method of treating an eosinophilic disease or disorder in a subject, the method comprising administering the antibody formulations described herein. In some embodiments, the invention is directed to treatment of pulmonary diseases or disorders e.g., asthma, COPD, eosinophilic asthma, combined eosinophilic and neutrophilic asthma, aspirin sensitive asthma, allergic bronchopulmonary aspergillosis, acute and chronic eosinophilic bronchitis, acute and chronic eosinophilic pneumonia, Churg-Strauss syndrome, hypereosinophilic syndrome, drug, irritant and radiation-induced pulmonary eosinophilia, infection-induced pulmonary eosinophilia (fungi, tuberculosis, parasites), autoimmune-related pulmonary eosinophilia, eosinophilic esophagitis, or Crohn's disease or combination thereof in a subject, the method comprising administering the antibody formulations described herein. In some embodiments, the invention is directed to treatment of asthma in a subject, the method comprising administering the antibody formulations described herein. In some embodiments, the invention is directed to treatment of COPD in a subject, the method comprising administering the antibody formulations described herein.

In some embodiments, a therapeutically effective amount of the antibody formulations described herein is administered to treat a condition. As used herein, the term "therapeutically effective amount" refers to the amount of a therapy (e.g., an antibody that immunospecifically binds to an IFNAR1 receptor polypeptide), that is sufficient to reduce the severity of a disease or disorder (e.g., a disease or disorder characterized by aberrant expression and/or activity of an IFNAR1 polypeptide, a disease or disorder characterized by aberrant expression and/or activity of an IFNAR1 receptor or one or more subunits thereof, an autoimmune disease, an inflammatory disease, a proliferative disease, or an infection or one or more symptoms thereof), reduce the duration of a condition, ameliorate one or more symptoms of such a disease or disorder, prevent the advancement of such a disease or disorder, cause regression of such a disease or disorder, or enhance or improve the therapeutic effect(s) of another therapy. In some embodiments, the therapeutically effective amount cannot be specified in advance and can be determined by a caregiver, for example, by a physician or other healthcare provider, using various means, for example, dose titration. Appropriate therapeutically effective amounts can also be determined by routine experimentation using, for example, animal models.

The terms "therapies" and "therapy" can refer to any protocol(s), method(s), and/or agent(s) that can be used in the prevention, treatment, management, or amelioration of a disease or disorder (e.g., a disease or disorder characterized by aberrant expression and/or activity of an IFNAR1 polypeptide, a disease or disorder characterized by aberrant expression and/or activity of an IFNAR1 receptor or one or more subunits thereof, an autoimmune disease, an inflammatory disease, a proliferative disease, or an infection (preferably, a respiratory infection) or one or more symptoms thereof). In certain embodiments, the terms "therapy" and "therapy" refer to biological therapy, supportive therapy, and/or other therapies useful in treatment, management, prevention, or amelioration of such a disease or disorder or one or more symptoms known to skilled medical personnel.

As used herein, the term "therapeutic protocol" refers to a regimen for dosing and timing the administration of one or more therapies (e.g., therapeutic agents) that has a therapeutic effective.

The route of administration of the antibody formulation of the present invention can be via, for example, oral, parenteral, inhalation or topical modes of administration. The term parenteral as used herein includes, e.g., intravenous, intraarterial, intraperitoneal, intramuscular, subcutaneous, rectal or vaginal administration. In some embodiments, the antibody is an anti-IFNAR1 antibody and the route of administration is intramuscular injection. While all these forms of administration are clearly contemplated as being within the scope of the invention, in some embodiments, the antibody formulation is suitable for administration via injection, in particular for intravenous or intraarterial injection or drip.

In some embodiments, the compositions and methods of the present invention enable a manufacturer to produce an antibody formulation suitable for administration to a human in a more efficient manner, either by reducing costs, reducing method steps, reducing opportunities for error, reducing opportunities for introduction of unsafe or improper additives, reducing waste, increasing storage time, etc.

EXAMPLES

The invention is now described with reference to the following examples. These examples are illustrative only and the invention should in no way be construed as being limited to these examples but rather should be construed to encompass any and all variations which become evident as a result of the teachings provided herein.

Example 1

Materials and Methods

Materials

All the materials used were of USP or Multicompendial grade. All the solutions and buffers were prepared using USP or HPLC water and were filtered before further use. Samples for stability studies were prepared under aseptic conditions in the Biosafety Cabinet Hood (BSC). Bulk material was stored at 2-8° C. Stability studies were carried out using the supplies listed in TABLE 3.

TABLE 3

| Component | Purification process |
| --- | --- |
| MEDI-546 | From cNS0 19B4 clone cell line |
| Vials | 3 cc Fiolax vials (Schott, p/n: 1230392) |
| Stoppers | West 13 mm HBR Teflon2 442/50 grey rubber stopper (item#:10124671) |
| Overseals | 13 mm aluminium TruEdge ® Flip-Off ® |

Protein Concentration Determination

Protein concentrations were determined by measuring absorbance at 280 nm with an Agilent UV-Vis spectrophotometer using a procedure adapted from SOP DV-6233. A measured extinction coefficient of 1.39 (mg/mL)-~cm~ was used. For the samples, density correction factors were applied as per TD-0025 for sugar or non-sugar containing formulations.

Cone and Plate Viscosity Measurements

Viscosities were measured using an Anton Paar MCR301 Rheometer with cone and plate accessory. To minimize volume required a 20 mm cone was used with single replicate measurements for screening purposes. Results were reported at the high-shear limit of 1000 per second shear rate.

Purity Determination by Size Exclusion Chromatography (HPSEC)

SEC analysis was performed on an Agilent HPLC system with a TSK-Gel G3000 as per the current Formulation Sciences guidelines.

Visual Appearance

Visual inspection of the samples were performed by examining the samples in their respective container for particles, color, and clarity using particle standards and guidance adapted from the standard operating procedure: Visual Appearance Evaluation of Protein Drug Substance and Drug Product.

Studies to Assess Impact of Excipient Levels on Stability and Viscosity

In order to study the impacts of concentration, trehalose level and lysine HCl level (factors) on stability and viscosity (responses) a design of experiments approach was utilized. A Box Behnken design was prepared using JMP9.1 software (SAS, Inc., Cary, N.C.). The design included factors: concentration (from 100 to 200 mg/mL); trehalose level (from 0 to 211 mM); and lysine HCL level (from 25 to 130 mM). The pH was set to 6.0 based on the previous formulation stability data for the cycle 1 formulations. The polysorbate level was set at 0.02%. The low lysine level was defined at 25 mM based on prelminary high-throughput viscosity screening studies where a large drop in viscosity over the range 0 to 25 mM lysine HCl was observed at high concentrations (see Example 2). Stability was evaluated by performing an accelerated stability study at 40° C. with assessment of visual appearance and purity by HP-SEC (monomer loss, aggregation, fragmentation) as readouts. Subvisible particle counts at 5° C. after 1.8 months were also measured but not further analyzed because no meaningful differentiation was observed between samples.

Robustness and Impact of Lysine HCl Level on Viscosity Profile

A stock of MEDI-546 at ~200 mg/mL in 25 mM histidine/histidine HCl, 25 mM lysineHCl (note: this is the low lysine HCl bracket), 130 mM trehalose dihydrate, pH 6.0 was prepared and used to prepare a dilution series formulated with 0.02% polysorbate 80. The concentration and viscosities were measured and plotted. The nominal formulation condition (50 mM lysine HCl) was also prepared and measured. A 0.5 M lysineHCl stock was prepared as used to spike the MEDI-546 stock to the nominal 50 mM lysine level. The same dilution and formulation was performed and the viscosities and concentrations were measured.

Assessment of Functionality of the Lead Formulation in 27 Ga STW Prefilled Syringes Prefilled syringes ("PFS") (BD Hypak SCF 1MLL 27 G1/2-SB); 0.4 mg silicone oil MDN with 27 G STW thin-wall needle) were filled with MEDI-546 at 150 mg/mL in 25 mM histidine/histidineHCl, 50 mM lysine HCl, 130 mM trehalose dihydrate, 0.05% polysorbate 80, pH 5.9. The viscosity of this lot was measured as 9.4 mPas and the concentration as 150.7 mg/mL. BD Hypak SCF 1MLL 4023 FLUR Daikyo SI1000 stoppers were applied with vacuum stoppering. An Instron 5542 (Norwood, Mass. 02062) was used to measure the gliding performance at 260 mm/min. Additionally, three analysts assessed the time to inject with and without arthritis simulation gloves (Arthritis gloves from Georgia Tech Research Institute and Injection trainer from Limbsnthings, UK).

Example 2

High-Throughput Viscosity Screening Results Summaries

High-throughput viscosity screening was performed with nanoparticles. In brief, nanoparticles of known size were measured in water (known viscosity) and the samples (unknown viscosity) and the ratio used to determine the unknown viscosity of the samples. These data were collected for screening and trending purposes and not for absolute viscosity determination.

Figure 2:
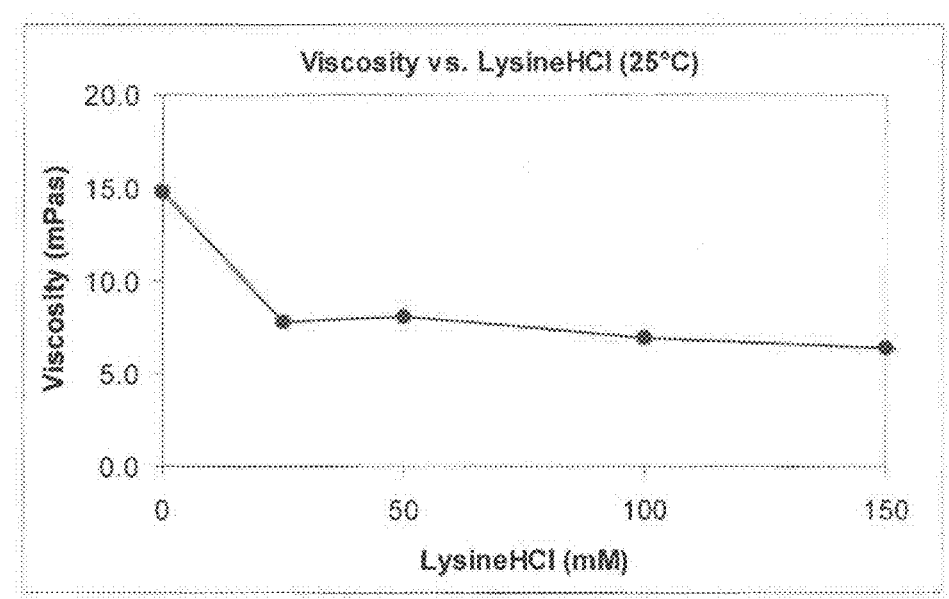
FIG. 2 shows viscosity as a function of lysine HCl concentration using a high throughput screening bead-based method.

The HTS screening results for viscosity vs. pH is shown in FIG. 1. The results suggested that viscosity increased with pH. Based on this potential impact of pH on the viscosity and possible Dorman-type effects during TFF we made the judgment that the formulation pH should be selected at 5.9. For PFS development additional robustness around the impact of pH will need to be performed. The HTS screening results for viscosity vs. lysine HCl (FIG. 2) showed a large drop in viscosity from zero to 25 mM lysine HCl. Hands-on laboratory observations of sample preparation also indicated that without lysine samples were more viscous and harder to handle at higher concentrations. For this reason the experiments started with 25 mM lysine HCl as the low level.

Example 3

Overall Assessment of Stability and Viscosity Results for the Formulations

TABLE 4 gives a summary of viscosity and accelerated stability results for the antibody formulations. TABLE 5 gives a summary of the subvisible particles results (by HIAC) for Formulations after 1.8 months at 5° C. An overall assessment of the results show that the purity loss rates at 40° C. were all acceptable, ranging from 3.8 to 4.8 percent per month. The fragmentation rate ranged from 2.8 to 3.4 percent per month and the aggregation rate ranged from 0.7 to 2.0 percent per month. The visual inspections after 1 month at 40° C. indicate similar performance for all formulations (all were standard 1 for particles, <III or II for clarity and Y6 for color). The subvisible particle (HIAC) data showed that all samples had less than 670 particles per mL greater than 10 microns in size. The viscosity ranged from 2.8 to 39.7 mPas for all of the formulations. Several of the formulations at 150 mg/mL had acceptable viscosity values.

Additional analysis of the data in the Examples below shows how the data was used and interpreted to select an appropriate and robust formulation that maximizes stability while providing an acceptable viscosity.

TABLE 4

Summary of Viscosity and Accelerated Stability Results for Formulations

| DOE ID | LysineHCl (mM) | Trehalose (mM) | Target Conc. (mg/mL) | Viscosity (mPa · s) | Aggregation Rate at 40° C. (%/month) | Fragmentation Rate at 40° C. (%/month) | Purity Loss Rate at 40° C. (%/month) | Visual Appearance After 1 month at 40° C. (particles, color, clarity) |
|---|---|---|---|---|---|---|---|---|
| 1 | 130 | 211 | 150 | 13.8 | 1.1 | 2.8 | 3.8 | 1, Y6, <III |
| 2 | 77.5 | 105.5 | 150 | 11.5 | 1.4 | 2.9 | 4.4 | 1, Y6, <III |
| 5 | 130 | 105.5 | 200 | 25.9 | 1.5 | 2.9 | 4.4 | 1, Y6, <III |
| 6 | 77.5 | 0 | 100 | 2.8 | 1.3 | 3.1 | 4.5 | 1, Y6, <III |
| 7 | 25 | 105.5 | 200 | 29.6 | 1.9 | 2.8 | 4.7 | 1, Y6, <III |
| 8 | 130 | 0 | 150 | 9.8 | 1.5 | 3.0 | 4.5 | 1, Y6, <III |
| 9 | 77.5 | 105.5 | 150 | 12.6 | 1.4 | 2.9 | 4.3 | 1, Y6, <III |
| 10 | 77.5 | 105.5 | 150 | 12.8 | 1.5 | 2.9 | 4.4 | 1, Y6, II |
| 11 | 130 | 105.5 | 100 | 4.0 | 1.1 | 3.0 | 4.1 | 1, Y6, <III |
| 12 | 77.5 | 0 | 200 | 39.7 | 2.0 | 2.8 | 4.8 | 1, Y6, <III |
| 13 | 25 | 0 | 150 | 12.1 | 1.7 | 2.8 | 4.6 | 1, Y6, <III |
| 14 | 25 | 211 | 150 | 16.7 | 1.3 | 2.9 | 4.2 | 1, Y6, II |
| 15 | 77.5 | 211 | 200 | 33.9 | 1.3 | 2.9 | 4.2 | 1, Y6, <III |
| 16 | 25 | 105.5 | 100 | 4.1 | 0.9 | 3.4 | 4.3 | 1, Y6, <III |
| 17 | 77.5 | 211 | 100 | 5.1 | 0.7 | 3.3 | 4.0 | 1, Y6, <III |

TABLE 5

Summary of Subvisible Particles Results for Formulations after 1.8 months at 5° C.

| DOE ID | LysineHCl (mM) | Trehalose (mM) | Target Conc. (mg/mL) | SVP ≥2 µm (HIAC) per mL | SVP ≥10 µm (HIAC) per mL | SVP ≥25 µm (HIAC) per mL |
|---|---|---|---|---|---|---|
| 1 | 130 | 211 | 150 | 880 | 20 | 0 |
| 2 | 77.5 | 105.5 | 150 | 2640 | 80 | 20 |
| 5 | 130 | 105.5 | 200 | 3493 | 0 | 0 |
| 6 | 77.5 | 0 | 100 | 4120 | 80 | 0 |
| 7 | 25 | 105.5 | 200 | 3627 | 53 | 0 |
| 8 | 130 | 0 | 150 | 4540 | 60 | 20 |
| 9 | 77.5 | 105.5 | 150 | 5940 | 220 | 40 |
| 10 | 77.5 | 105.5 | 150 | 5640 | 20 | 0 |
| 11 | 130 | 105.5 | 100 | 1387 | 67 | 0 |
| 12 | 77.5 | 0 | 200 | 1680 | 53 | 0 |
| 13 | 25 | 0 | 150 | 1691 | 40 | 0 |
| 14 | 25 | 211 | 150 | 3980 | 20 | 0 |
| 15 | 77.5 | 211 | 200 | 44853 | 667 | 53 |
| 16 | 25 | 105.5 | 100 | 5800 | 93 | 13 |
| 17 | 77.5 | 211 | 100 | 5440 | 120 | 13 |

Example 4

Analysis of Results

TABLE 6 summarizes the interpretation and conclusions drawn from the data:

TABLE 6

Output for Significance of Factors on Measured Responses

| | Concentration | Lysine HCl Level | Trehalose Level |
|---|---|---|---|
| Viscosity Results | Significant Impact: Viscosity increased with concentration. | Not significant (for range tested above 25 mM) | Not significant. Minor trend for increase in viscosity with higher trehalose. |
| Viscosity Conclusions | Data suggests 150 mg/mL is feasible (<20 mPas) but that 200 mg/mL will have too high a viscosity (>30 mPas). Lysine was shown to decrease viscosity in prior work. A bracket with 25 mM as the low end and 50 mM as the nominal level would provide appropriate robustness. | | |
| Aggregation Rate | Significant: aggregation increased with concentration | Not significant | Significant: trehalose decreased aggregation by a small amount. |
| Aggregation Rate Conclusions | Strategy to maximize trehalose with isotonic constraint (little incremental benefit of much higher trehalose was observed to justify hypertoncity) will minimize aggregation. | | |
| Fragmentation Rate | Significant: fragmentation slightly decreased with concentration. Rate ranged from 2.8 to 3.4 percent per month at 40° C. | Not significant | Not significant |
| Fragmentation Rate Conclusions | Fragmentation is not likely an issue over entire knowledge space at 5° C. Differences in rate were very minor and could be artifacts of method variability due to SEC shoulder 'pop' on stability. | | |
| Overall Conclusions. | Overall, a lead formulation at 150 mg/mL with 50 mM lysineHCl to minimize viscosity and 130 mM trehalose to minimize aggregation will achieve isotonic condition when 25 mM histidine buffer is present. Polysorbate level will require additional optimization. | | |

Based on the analysis results, a formulation having MEDI-546 at 150 mg/mL in 25 mM histidine/histidine HCl, 50 mM lysine HCl, 130 mM trehalose dehydrate, 0.05% polysorbate 80 and a pH of 5.9 was further assessed.

Example 6

Confirmation of Viscosity and Syringe Functionality for Antibody Formulation

Ideally the glide force for a prefilled syringe should be as low as possible to ensure functionality. In this work we are targeting a viscosity of less than 20 mPas and a glide force of less than 15 N. Prior experience has been for formulations with nominal viscosities less than 15 mPas to have acceptable gliding performance when equipped with 27 Gauge thin-walled needles. Up to 20 mPas may be feasible in 27 Ga STW PFS. The formulation and PFS should include robustness to account for variability in the syringes and the formulation.

In this section we document additional data demonstrating the robustness of a formulation viscosity vs. concentration curve when compared with a lower bracket (25 mM) lysine-HCl formulation. Gliding performance and injection time feasibility results with the nominal formulation in 27 Ga STW PFS are also assessed in this section.

Robustness and Impact of Lysine HCl Level on Viscosity Profile

Figure 3:
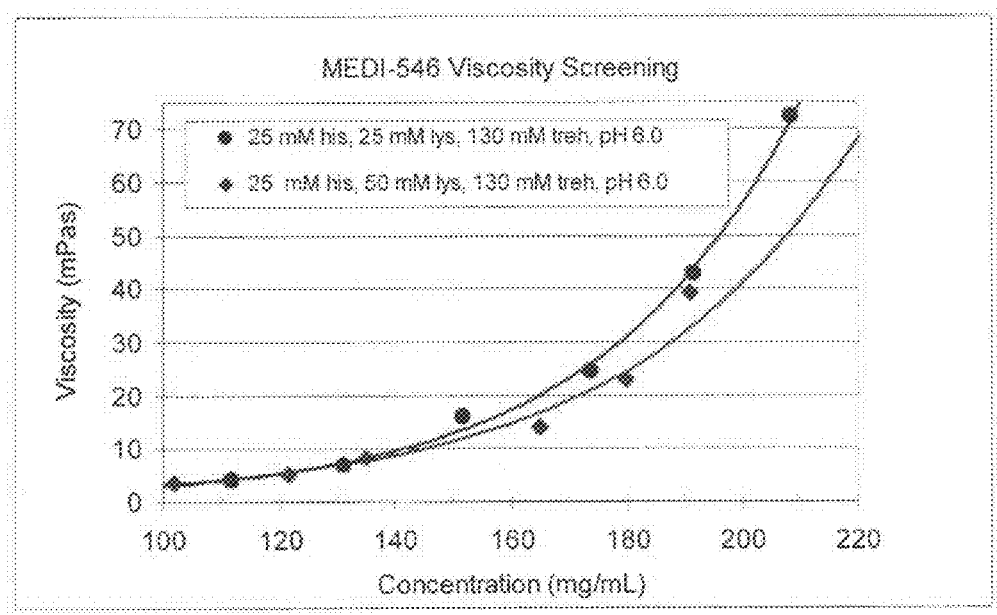
FIG. 3 shows viscosity as a function of concentration of antibody (anifrolumab) concentration for formulations containing 25 mM histidine/histidine-HCl, 25 mM lysine, 130 mM trehalose at pH 6.0 (circles); and 25 mM histidine/histidine-HCL, 50 mM lysine, 130 mM trehalose at pH 6.0 (diamonds).

A dilution series of MEDI-546 over 100 to 200 mg/mL was prepared in two formulations. They contained MEDI-546 in 25 mM histidine/histidine-HCl, 130 mM trehalose dehydrate with 0.02% polysorbate 80 at pH 6.0 with either 25 mM or 50 mM lysine HCl. The viscosity curves are shown in FIG. 3. The results show that the viscosity of the formulations with both low (25 mM) and nominal (50 mM) lysine levels is acceptable at 150 mg/mL (<15 mPas) and that they are both below about 20 mPas at 165 mg/mL. Therefore the results that the nominal level of 50 mM lysine HCl is appropriately bracketed by the 25 mM lower level in terms of viscosity performance were confirmed. Based on the impact of pH on the viscosity and possible Dorman-type effects during TFF the antibody formulation pH was selected to be 5.9.

Assessment of Functionality of the Antibody Formulation in Prefilled Syringes

Table 7 gives the results of the functionality assessment of a formulation having MEDI-546 at 150 mg/mL in 25 mM histidine/histidine HCl, 50 mM lysine HCl, 130 mM trehalose dehydrate, 0.05% polysorbate 80 and a pH of 5.9.

The forces required to inject MEDI-546 Drug Product were within acceptable ranges. Table 8 gives the results of the user injection assessment (laboratory analysts). The users reported that 'Injection Force was easy'; 'arthritis gloves made handling of the APFS difficult'; 'SSI device worked.' Some variability in injection speed was noted based on users being new to using injection trainer and gloves (note: force to inject was not considered an issue). These results indicate that this formulation is suitable for use in a PFS with a 27 Ga STW needle. These studies did not identify any issues with the viscosity of the antibody formulations.

TABLE 7

Functionality Assessment of Antibody Formulation

| Replicate | Break Loose Force (N) | Average Glide Force (N) | Max. Glide Force (N) | Abs. Max. Force (N) |
|---|---|---|---|---|
| 1 | 8.0 | 7.3 | 8.0 | 8.5 |
| 2 | 7.0 | 8.7 | 9.1 | 9.1 |
| 3 | 7.8 | 7.7 | 8.2 | 8.5 |

TABLE 8

User Injection Time Assessment

| Analyst | Injection time(s) - using arthritis gloves and APFS (flange, SSI device) | Injection time(s) - bare PFS |
|---|---|---|
| 1 | 9.8 | 15.6 |
| 2 | 17 | 10.4 |
| 3 | 8.1 | 5.9 |

Example 7

Lysine and Protein Effects on Viscosity

Figure 4:
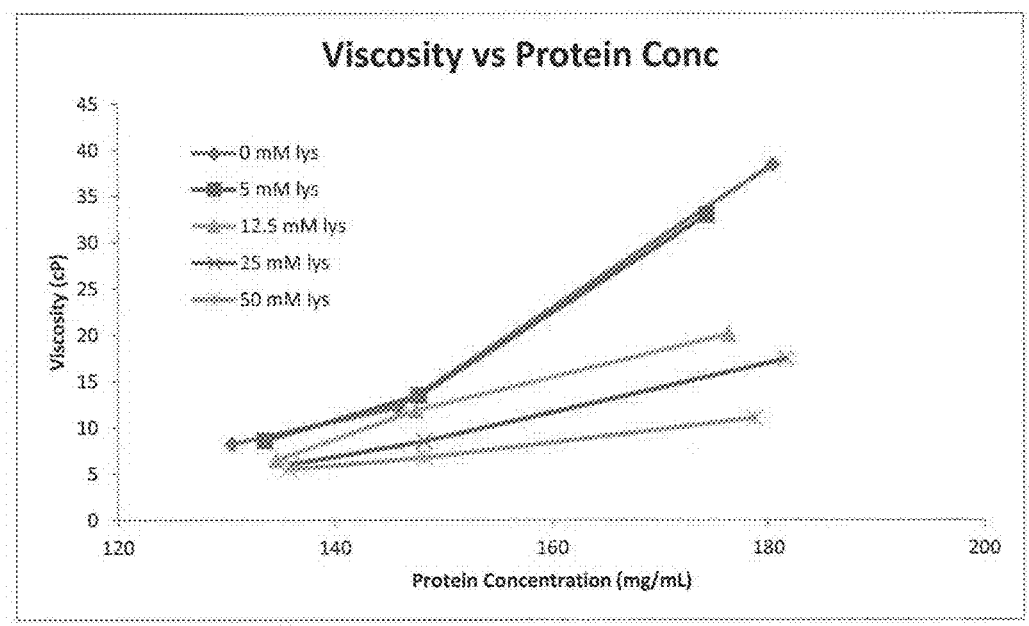
FIG. 4 shows viscosity as a function of antibody (anifrolumab) concentration for solutions containing: 0 mM lysine (diamonds); 5 mM lysine (squares); 12.5 mM lysine (triangles); 25 mM lysine (x's); and 50 mM lysine (asterisks).

The viscosity of solutions of lysine at different concentrations were measured as a function of protein (anifrolumab) concentration, as shown in Table 9 and FIG. 4.

TABLE 9

| conc (mg/mL) | viscosity (cP) |
|---|---|
| 0 mM lysine | |
| 130.5 | 8.3 |
| 145.8 | 12.3 |
| 180.5 | 38.4 |
| 5 mM lysine | |
| 133.5 | 8.6 |
| 147.8 | 13.5 |
| 174.4 | 33.0 |
| 12.5 mM lysine | |
| 134.6 | 6.6 |
| 147.5 | 11.9 |
| 176.4 | 20.1 |
| 25 mM lysine | |
| 135.9 | 6.1 |
| 148.2 | 8.6 |
| 181.6 | 17.5 |
| 50 mM lysine | |
| 135.8 | 5.6 |
| 148.3 | 6.8 |
| 178.8 | 11.1. |

Figure 5:
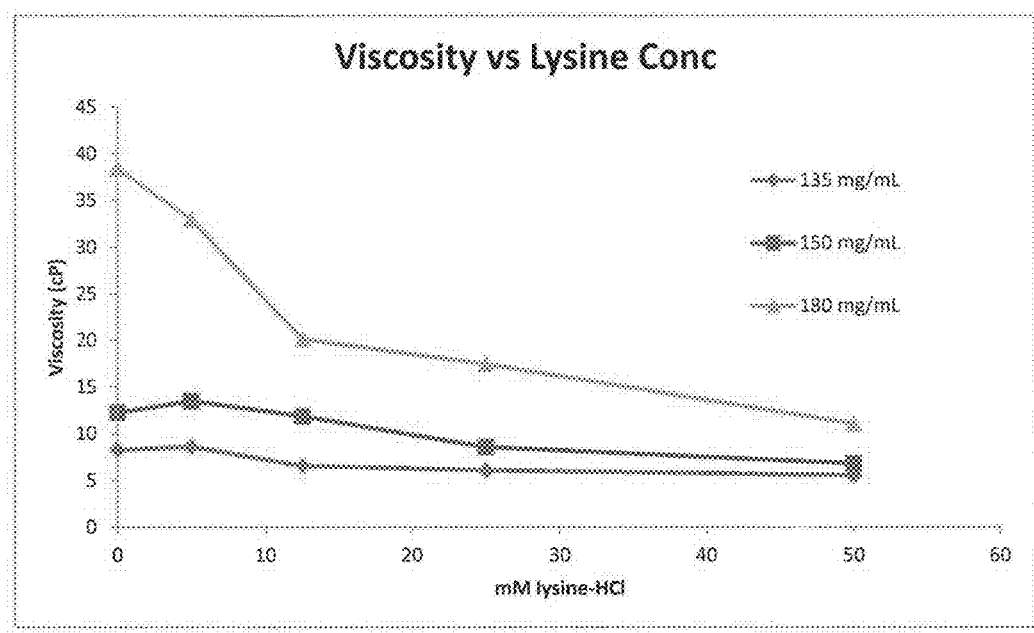
FIG. 5 shows viscosity as a function of lysine HCl concentration for solutions containing: 135 mg/mL anifrolumab (diamonds); 150 mg/mL anifrolumab (squares); and 180 mg/mL anifrolumab (triangles).

The viscosity of solutions of antibody (anifrolumab) at different concentrations were measured as a function of protein concentration, as shown Table 10 and FIG. 5.

TABLE 10

| mM lysine | viscosity (cP) |
|---|---|
| Target 135 mg/mL | |
| 0 | 8.3 |
| 5 | 8.6 |
| 12.5 | 6.6 |
| 25 | 6.1 |
| 50 | 5.6 |
| Target 150 mg/mL | |
| 0 | 12.3 |
| 5 | 13.5 |
| 12.5 | 11.9 |
| 25 | 8.6 |
| 50 | 6.8 |
| Target 180 mg/mL | |
| 0 | 38.4 |
| 5 | 33.0 |
| 12.5 | 20.1 |
| 25 | 17.5 |
| 50 | 11.1 |

The examples shown above illustrate various aspects of the invention and practice of the methods of the invention. These examples are not intended to provide an exhaustive description of the many different embodiments of the invention. Thus, although the invention has been described in some detail by way of illustration and example for purposes of clarity of understanding, those of ordinary skill in the art will realize readily that many changes and modifications can be made without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. An antibody formulation comprising:
   a. 150 mg/mL anifrolumab;
   b. 50 mM lysine HCl;
   c. 130 mM trehalose dihydrate;
   d. 0.05% polysorbate 80;
   e. 25 mM histidine/histidine HCl,
   wherein the formulation is at a pH of 5.9.

2. The antibody formulation of claim 1, wherein the formulation is an injectable formulation suitable for intravenous, subcutaneous, or intramuscular administration.

3. A pre-filled syringe comprising:
 a. 150 mg/mL anifrolumab;
 b. 50 mM lysine HCl;
 c. 130 mM trehalose dihydrate;
 d. 0.05% polysorbate 80;
 e. 25 mM histidine/histidine HCl
wherein the formulation is at a pH of 5.9.

* * * * *